United States Patent
Sauve

(10) Patent No.: US 11,530,233 B2
(45) Date of Patent: *Dec. 20, 2022

(54) BETA-NICOTINATE ESTER NUCLEOTIDES AND PROCESSES FOR PREPARING SAME

(71) Applicant: Cornell University, Ithaca, NY (US)

(72) Inventor: Anthony A. Sauve, New Rochelle, NY (US)

(73) Assignee: Cornell University, Ithaca, NY (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/216,533

(22) Filed: Mar. 29, 2021

(65) Prior Publication Data

US 2021/0214386 A1  Jul. 15, 2021

Related U.S. Application Data

(63) Continuation of application No. 16/603,164, filed as application No. PCT/US2018/026209 on Apr. 5, 2018, now Pat. No. 10,961,268.

(60) Provisional application No. 62/481,912, filed on Apr. 5, 2017.

(51) Int. Cl.
  *C07H 19/048* (2006.01)
  *C07F 9/6558* (2006.01)
  *C07H 1/02* (2006.01)

(52) U.S. Cl.
  CPC ....... *C07H 19/048* (2013.01); *C07F 9/65586* (2013.01); *C07H 1/02* (2013.01)

(58) Field of Classification Search
  None
  See application file for complete search history.

(56) References Cited

U.S. PATENT DOCUMENTS

| | | | |
|---|---|---|---|
| 3,736,314 A | 5/1973 | Jones et al. |
| 8,106,184 B2 | 1/2012 | Sauve et al. |
| 9,000,147 B2 | 4/2015 | Sauve et al. |
| 9,290,791 B2 | 3/2016 | Sauve et al. |
| 9,321,797 B2 | 4/2016 | Sauve et al. |
| 9,322,049 B2 | 4/2016 | Sauve et al. |
| 9,603,862 B2 | 3/2017 | Sauve et al. |
| 9,790,252 B2 | 10/2017 | Sauve et al. |
| 9,861,651 B2 | 1/2018 | Brown et al. |
| 10,206,940 B2 | 2/2019 | Sauve et al. |
| 10,392,414 B2 | 8/2019 | Sauve et al. |
| 10,525,070 B2 | 1/2020 | Andrews et al. |
| 10,590,160 B2 | 3/2020 | Sauve et al. |
| 10,668,096 B2 | 6/2020 | Sauve et al. |
| 10,961,268 B2 | 3/2021 | Sauve et al. |
| 2012/0108535 A1 | 5/2012 | Sauve et al. |
| 2012/0172584 A1 | 7/2012 | Sauve et al. |
| 2012/0329748 A1 | 12/2012 | Sauve et al. |
| 2013/0029930 A1 | 1/2013 | Sauve et al. |
| 2013/0065248 A1 | 3/2013 | Sauve et al. |
| 2015/0072950 A1 | 3/2015 | Sauve et al. |
| 2015/0174148 A1 | 6/2015 | Brown et al. |
| 2016/0310517 A1 | 10/2016 | Sauve et al. |
| 2016/0355539 A1 | 12/2016 | Migaud et al. |
| 2018/0208619 A1 | 7/2018 | Sauve et al. |
| 2018/0291054 A1 | 10/2018 | Sauve et al. |
| 2019/0038647 A1 | 2/2019 | Andrews et al. |
| 2019/0192542 A1 | 6/2019 | Sauve et al. |
| 2019/0382436 A1 | 12/2019 | Sauve et al. |
| 2020/0031860 A1 | 1/2020 | Sauve |
| 2020/0216487 A1 | 7/2020 | Sauve et al. |
| 2020/0289535 A1 | 9/2020 | Sauve et al. |

FOREIGN PATENT DOCUMENTS

| | | |
|---|---|---|
| WO | WO 2011/081942 A1 | 7/2011 |
| WO | WO 2014/014828 A1 | 1/2014 |
| WO | WO 2015/186114 A1 | 12/2015 |
| WO | WO 2016/130691 A1 | 8/2016 |
| WO | WO 2016/160524 A1 | 10/2016 |
| WO | WO 2017/011788 A1 | 1/2017 |
| WO | WO 2018/187540 A1 | 10/2018 |
| WO | WO 2020/072497 A1 | 4/2020 |

OTHER PUBLICATIONS

U.S. Appl. No. 11/601,714, filed Nov. 17, 2006.
U.S. Appl. No. 13/351,411, filed Jan. 17, 2012.
U.S. Appl. No. 13/381,587, filed Jul. 1, 2010.
U.S. Appl. No. 13/516,190, filed Dec. 14, 2010.
U.S. Appl. No. 13/516,198, filed Dec. 14, 2010.
U.S. Appl. No. 13/698,561, filed May 18, 2011.
U.S. Appl. No. 14/414,924, filed Jul. 15, 2013.
U.S. Appl. No. 14/543,439, filed Nov. 17, 2014.
U.S. Appl. No. 15/137,818, filed Apr. 25, 2016.
U.S. Appl. No. 15/550,150, filed Feb. 10, 2016.
U.S. Appl. No. 15/562,336, filed Mar. 24, 2016.
U.S. Appl. No. 15/744,602, filed Jul. 15, 2016.
U.S. Appl. No. 16/277,741, filed Feb. 15, 2019.
U.S. Appl. No. 16/551,401, filed Aug. 26, 2019.

(Continued)

*Primary Examiner* — Layla D Berry
(74) *Attorney, Agent, or Firm* — Leydig, Voit & Mayer, Ltd.

(57) ABSTRACT

The invention provides a compound of formula (I):

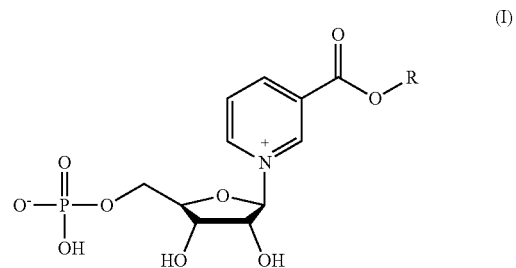

wherein R is as described herein. The invention also provides a process for the preparation of the compound.

24 Claims, 13 Drawing Sheets

(56) References Cited

OTHER PUBLICATIONS

U.S. Appl. No. 16/603,164, filed Oct. 4, 2019.
U.S. Appl. No. 16/820,548, filed Mar. 16, 2020.
U.S. Appl. No. 16/888,336, filed May 29, 2020.
Araki & Milbrandt, "Increased nuclear NAD biosynthesis and SIRT1 activation prevent axonal degeneration," *Science*, 305(5686): 1010-1013 (2004) [abstract only].
Berge et al., "Pharmaceutical Salts", *Journal of Pharmaceutical Science*, 66(1): 1-19 (1977).
C.H.R. Winne et al., "Synthesis of NAD+ Analogs, Part II, Synthesis and Anomeric Separation of 3-Benzoylpyridine Nucleotide," Bulletin Des Societes Chimeques Belges: Vlaamse Chemische Vereniging, vol. 92, No. 2, Jan. 1, 1983 (Jan. 1, 1983), pp. 175-180, XP055500759, BE.
Extended European Search Report dated Apr. 6, 2020 in European Patent Application No. 18781797.8 filed Apr. 5, 2018.
Jacobson, et al., "Pyridine Nucleotide Levels as a Function of Growth in Normal and Transformed 3T3 Cells", *Archives of Biochemistry and Biophysics*, 175: 627-634 (1976).
Lopez-Lluch, et al., "Mitochondrial Biogenesis and Healthy Aging," *Experimental Gerontology*, 43 (9): 813-819 (2009).
*Remington's Pharmaceutical Sciences*, 18th ed., Mack Publishing Company, Easton, PA, 1990, p. 1445.
U.S. Patent & Trademark Office, International Search Report in International Application No. PCT/US2018/026209 (dated Jun. 11, 2018).
Wang et al., "A local mechanism mediates NAD-dependent protection of axon degeneration," *J. Cell Biol.*, 170(3): 349-55 (2005).
Yoshikawa et al., "Studies of Phosphorylation. III. Selective Phosphorylation of unprotected Nucleosides", *Selective Phosphorylation of Unprotected Nucleosides, Bulletin of the Chemical Society of Japan*, 42: 3505-3508 (1969).

BETA-NICOTINATE ESTER NUCLEOTIDES AND PROCESSES FOR PREPARING SAME

CROSS REFERENCE TO A RELATED APPLICATION

This patent application is a continuation of copending U.S. patent application Ser. No. 16/603,164, filed Oct. 4, 2019, now issued as U.S. Pat. No. 10,961,268, which is the U.S. national stage of International Patent Application No. PCT/US2018/026209, filed Apr. 5, 2018, which claims the benefit of U.S. Provisional Patent Application No. 62/481,912, filed Apr. 5, 2017, which are incorporated by reference in their entireties for all purposes.

BACKGROUND OF THE INVENTION

Nicotinamide adenine dinucleotide (NAD) is an important co-enzyme and substrate in several biological pathways and biochemical reactions including ADP-ribosylation and protein deacetylation and as an essential redox co-factor for many enzymes.

NAD participation in metabolism makes it an important metabolite in several biological processes, such as aging, apoptosis, DNA repair, transcriptional regulation, and immune response.

NAD can be synthesized from different precursors containing pyridine moieties in several salvage pathways (nicotinamide (Nam), nicotinic acid (NA), and nicotinamide riboside (NR)) and in the de novo pathway from tryptophan. Many non-mammalian organisms use nicotinic acid (a form of vitamin $B_3$) as a major NAD precursor. Mammals predominantly use nicotinamide (another form of vitamin $B_3$) for NAD biosynthesis. In bacteria and yeast, Nam is converted to NA by the enzyme nicotinamidase, but this enzyme is not encoded in mammal genomes.

Cellular NAD consumption is high, and variation in the cellular levels of NAD plays an important role in health and diseases like cancer, diabetes, neurodegenerative diseases, and autoimmune disorders. Constant recycling of NAD is crucial to sustain the activities of cellular enzymes. In mammals, particularly in humans, the main source of cellular NAD is from salvage pathways, which require the uptake or metabolism of NAD precursors (i.e., NAM, NA, nicotinate mononucleotide (NaMN), nicotinamide mononucleotide (NMN), and nicotinamide riboside (NR)) from the diet or via intracellular reuse after metabolism. Efficient chemical syntheses of these precursors are in high demand. U.S. Pat. No. 8,106,184 describes ester derivatives of nicotinic acid riboside and their ability to increase intracellular NAD in HeLa cells. Thus, stereoisomerically pure 5-phosphates of nicotinate ester ribosides may be effective to treat a disease or disorder that would benefit from increased NAD levels, including insulin resistance, obesity, diabetes, and metabolic syndrome. An efficient synthetic route to 5-phosphates of nicotinate ester ribosides is needed to obtain and evaluate such compounds for their utility as precursors to NAD.

A commonly practiced method for the synthesis of 5-ribotides from the corresponding ribosides employs a protection and deprotection strategy, which involves protection of secondary alcohols followed by phosphorylation of 5-hydroxy group and then deprotection of the secondary alcohols. This strategy is inefficient in terms of time, cost, and particularly yields.

Thus, there remains in the art a need for an efficient synthesis of 5-phosphates of nicotinate ester ribosides.

BRIEF SUMMARY OF THE INVENTION

The invention provides a process for the preparation of a compound of formula (I):

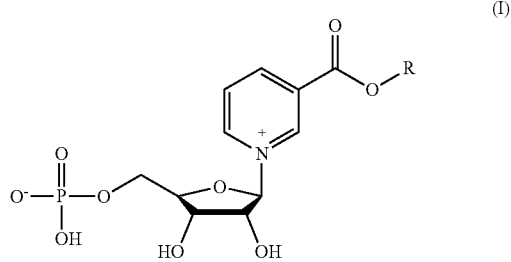

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof, wherein the process comprises the step of:

reacting a compound of formula (III):

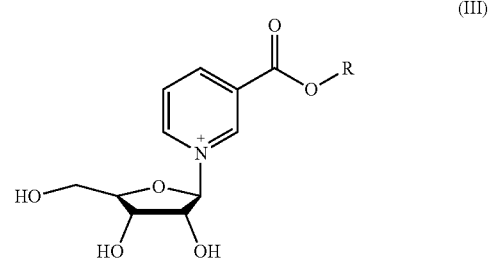

with a mixture of $POCl_3$ and $PO(OR^5)_3$, wherein $R^5$ is $C_1$-$C_6$ alkyl, followed by treatment with water to form the compound of formula (I).

The invention also provides a for the preparation of a compound of formula (I):

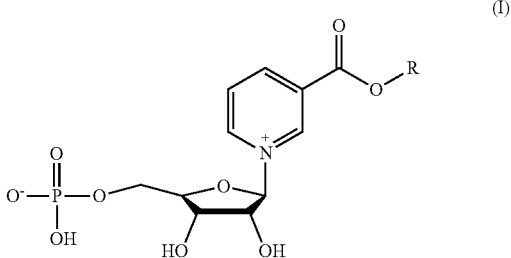

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:

(i) reacting a compound of formula (II):

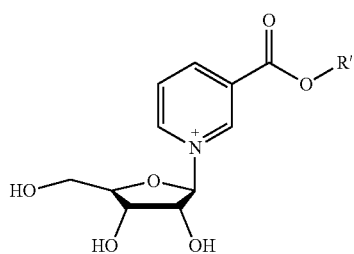

wherein R' is methyl or ethyl, with a compound of formula ROH in the presence of a base in a solvent to form a compound of formula (III):

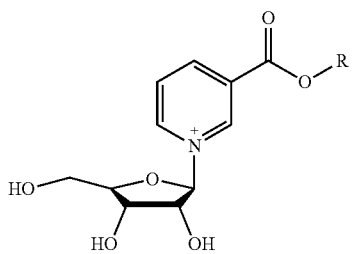

and
(ii) reacting the compound of formula (III) with a mixture of $POCl_3$ and $PO(OR^5)_3$, wherein $R^5$ is $C_1$-$C_6$ alkyl, followed by treatment with water to form the compound of formula (I).

The invention further provides a process for the preparation of a compound of formula (I):

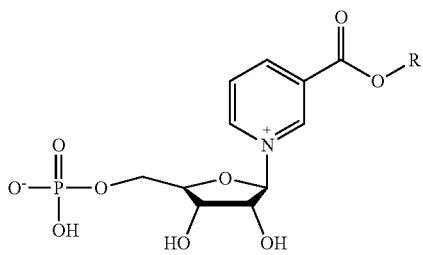

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:
(i) reacting a nicotinate ester (IV):

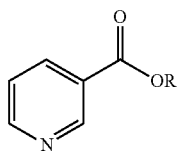

with 1,2,3,4-tetra-O-acetyl-D-ribofuranose to provide a compound of formula (V):

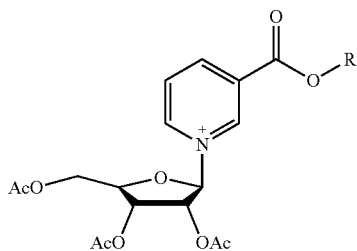

(ii) reacting the compound of formula (V) with a base to form the compound of formula (III):

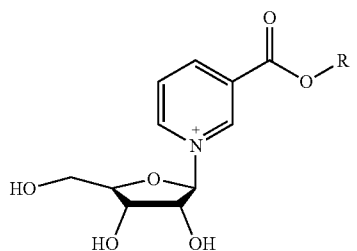

and
(ii) reacting the compound of formula (III) with a mixture of $POCl_3$ and $PO(OR^5)_3$, wherein $R^5$ is $C_1$-$C_6$ alkyl, followed by treatment with water to form the compound of formula (I).

The invention additionally provides a compound of formula (I):

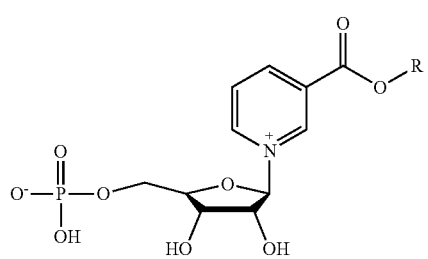

wherein R is straight or branched chain $C_3$-$C_{20}$ alkyl, straight or branched chain $C_2$-$C_{20}$ alkenyl, $C_2$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof, as well as a pharmaceutical composition comprising the aforementioned compound or salt thereof and a pharmaceutically acceptable carrier, and a nutraceutical composition comprising the aforementioned compound or salt thereof.

Furthermore, the invention provides a method for increasing cell $NAD^+$ production comprising administering to a cell the aforementioned compound or a salt thereof, and a method of improving mitochondrial densities in a cell comprising administering to the cell the aforementioned compound or a salt thereof.

BRIEF DESCRIPTION OF THE SEVERAL VIEWS OF THE DRAWING(S)

FIG. 1 is a $^1$H NMR spectrum of compound 5a.

FIG. 2 is a $^{13}$C NMR spectrum of compound 5a.

FIG. 3 is a $^{31}$P NMR spectrum of compound 5a.

Figure 6A:
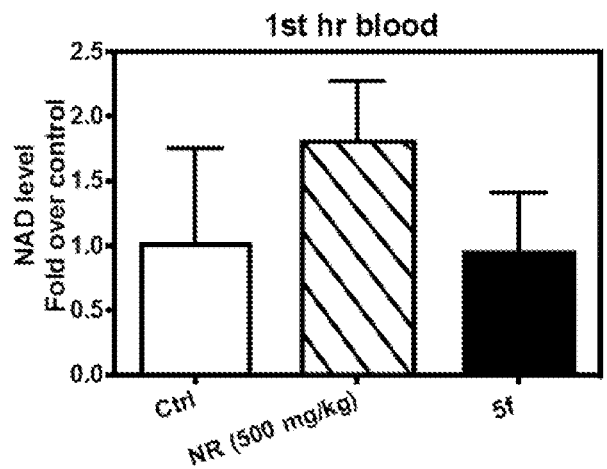
Figure 6B:
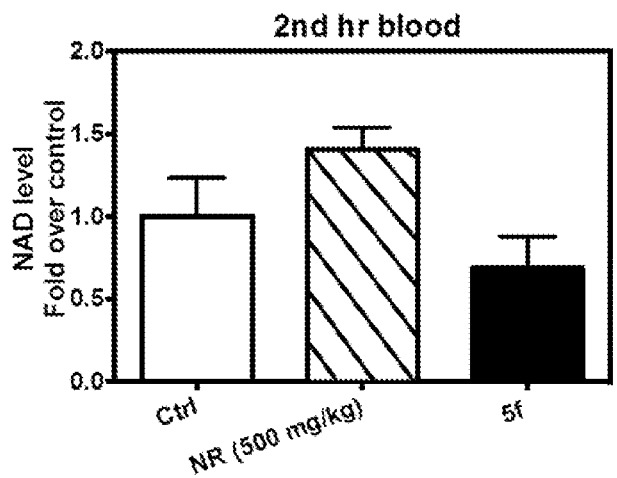
Figure 6C:
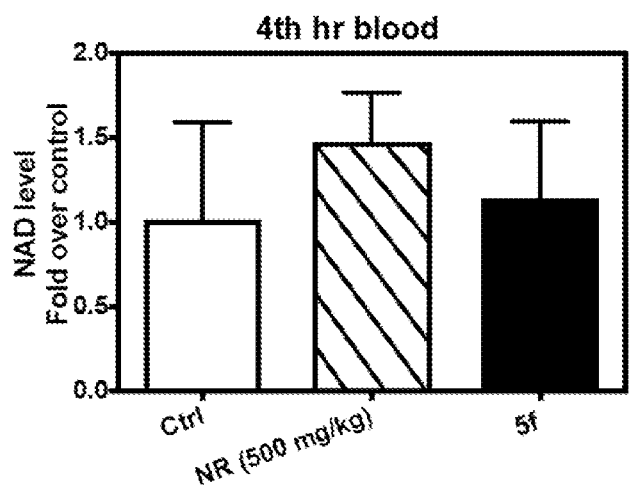
Figure 7A:
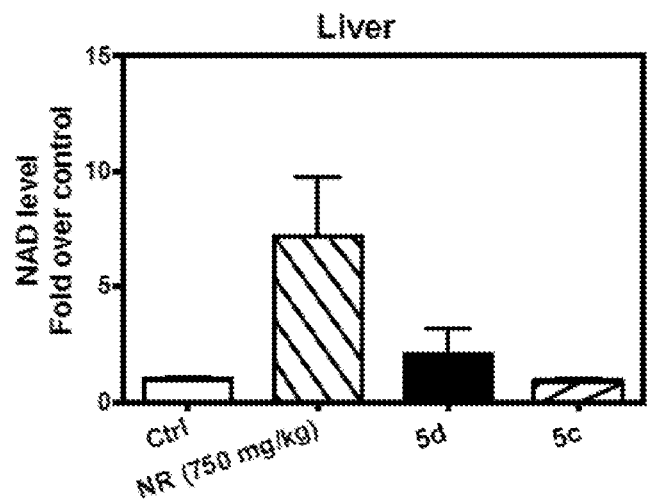
Figure 7B:
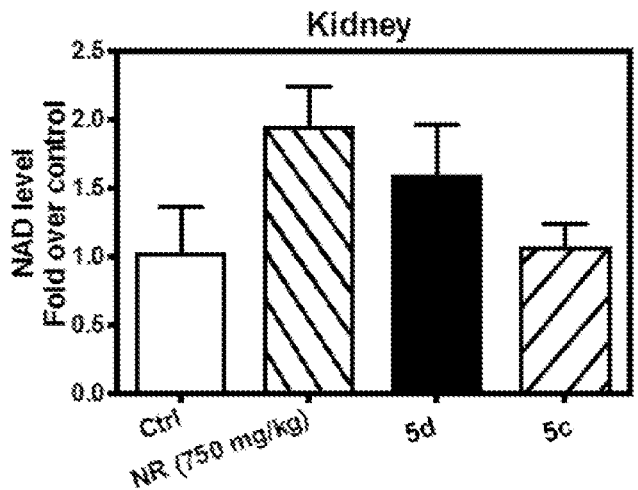
Figure 7C:
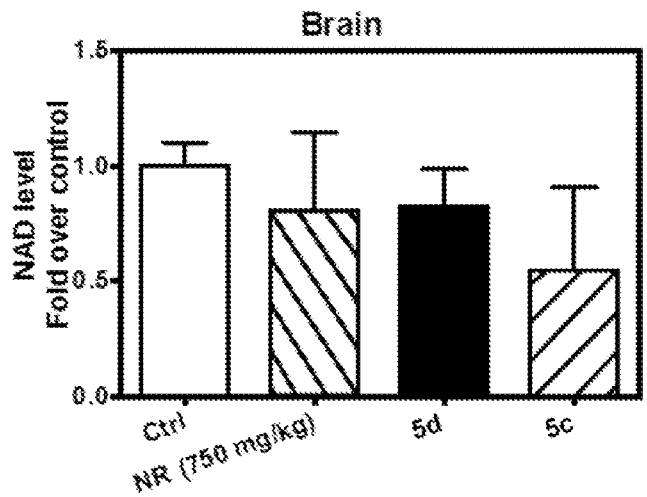
Figure 7D:
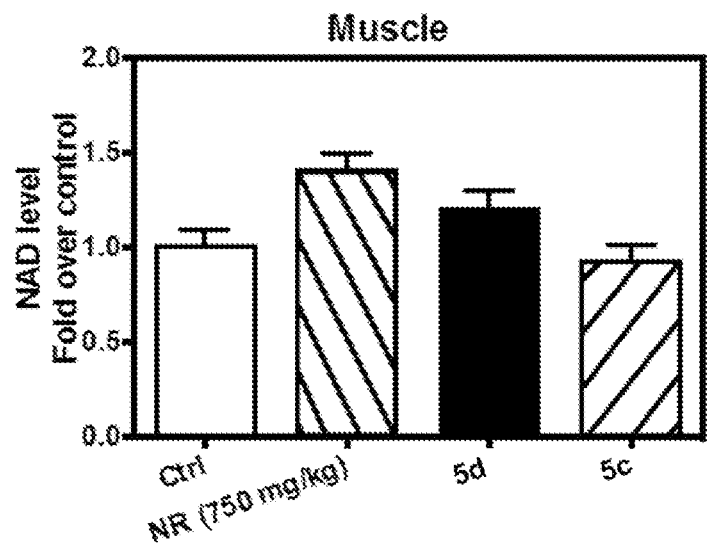
Figure 7E:
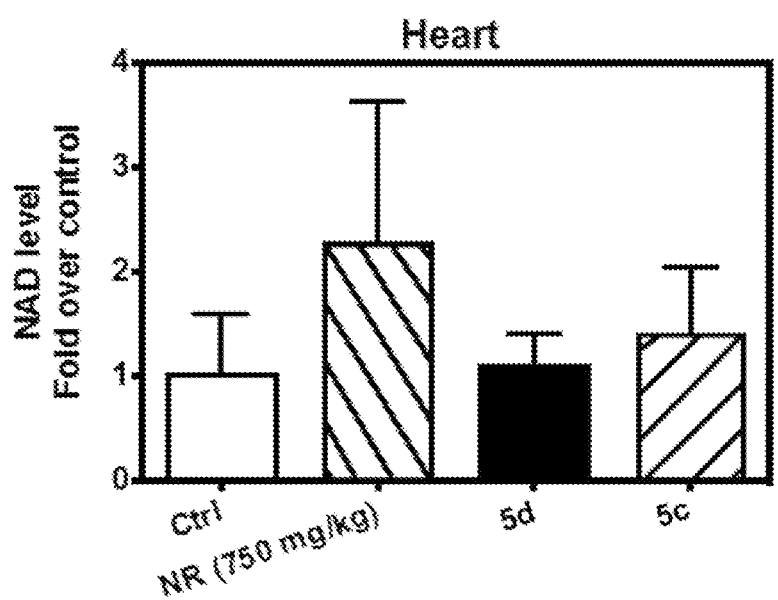
Figure 8A:
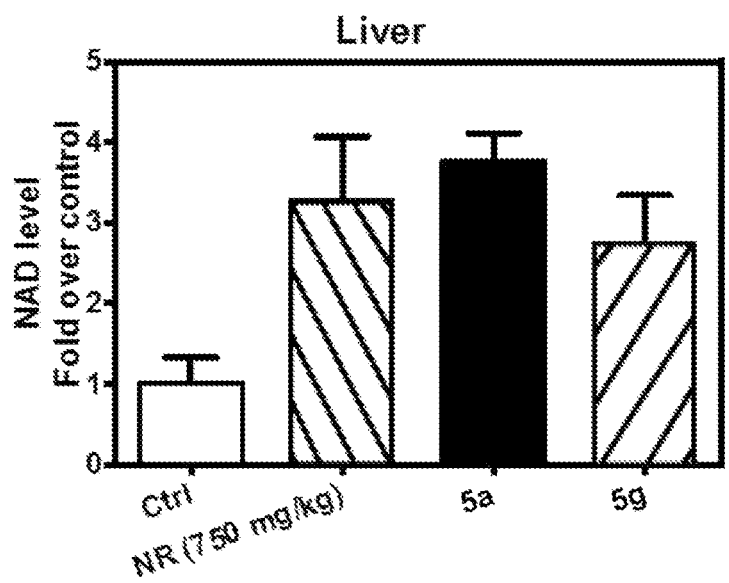
Figure 8B:
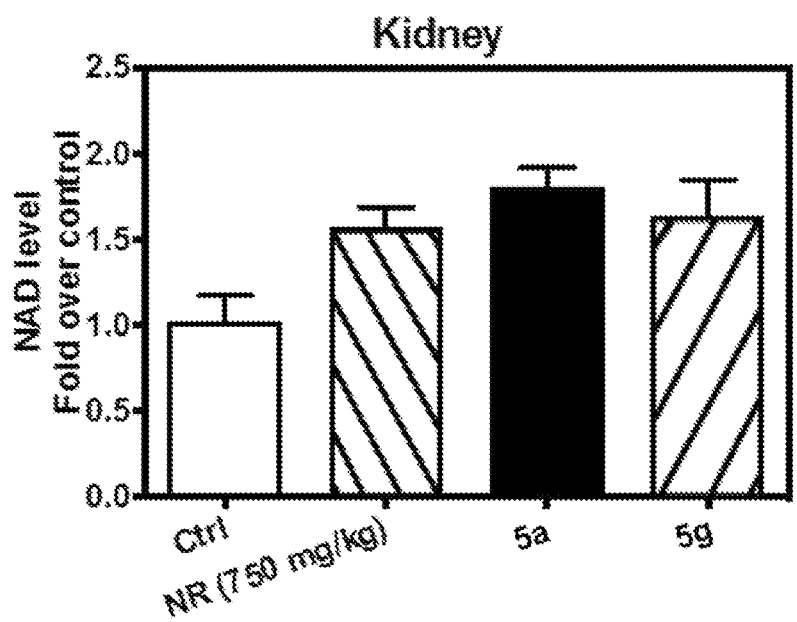
Figure 8C:
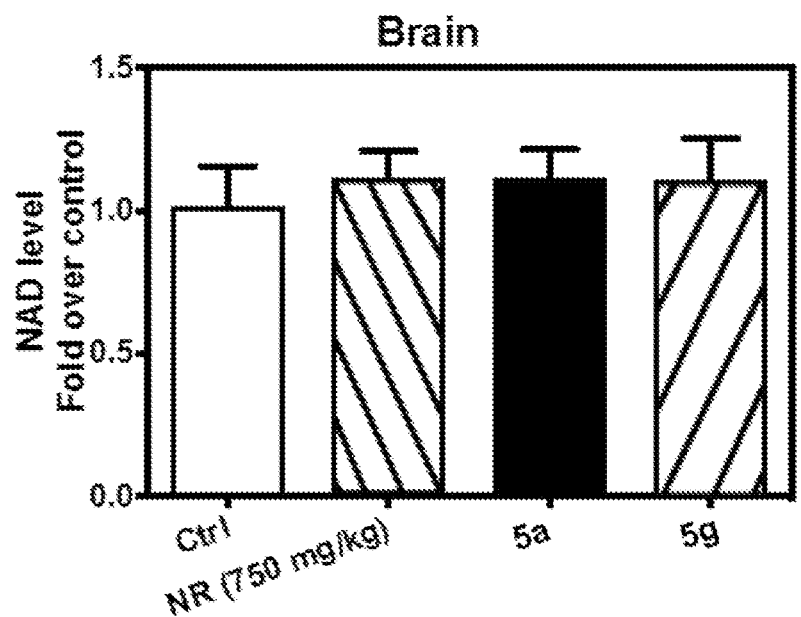
Figure 8D:
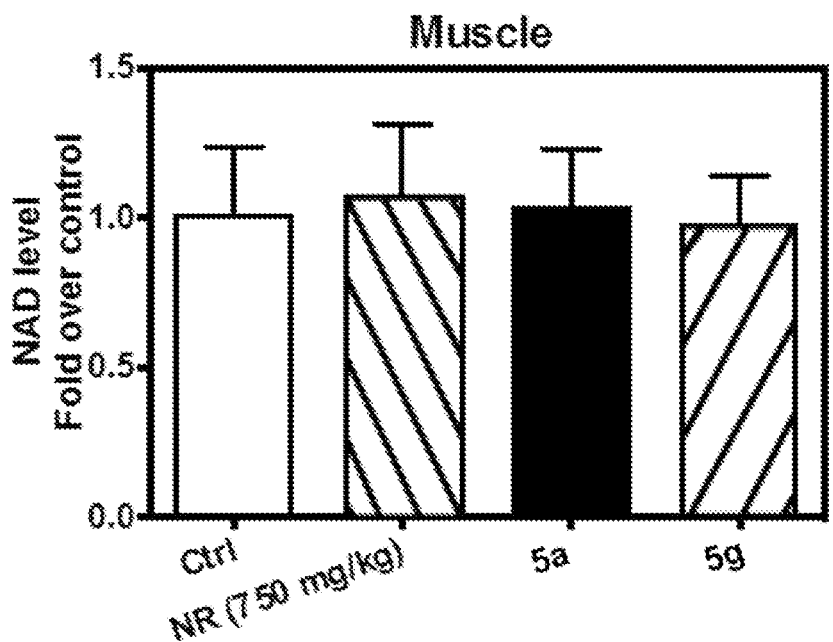
Figure 9A:
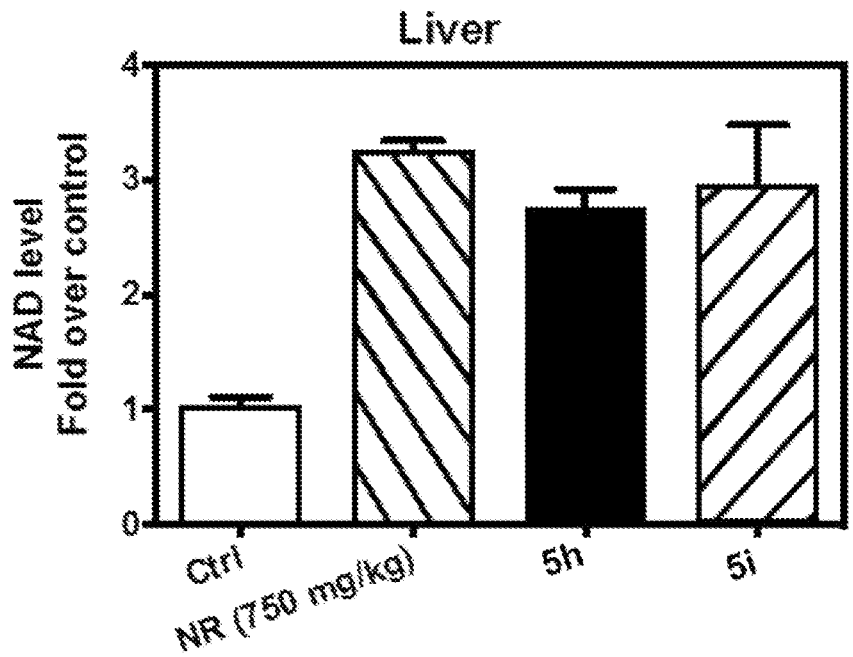
Figure 9B:
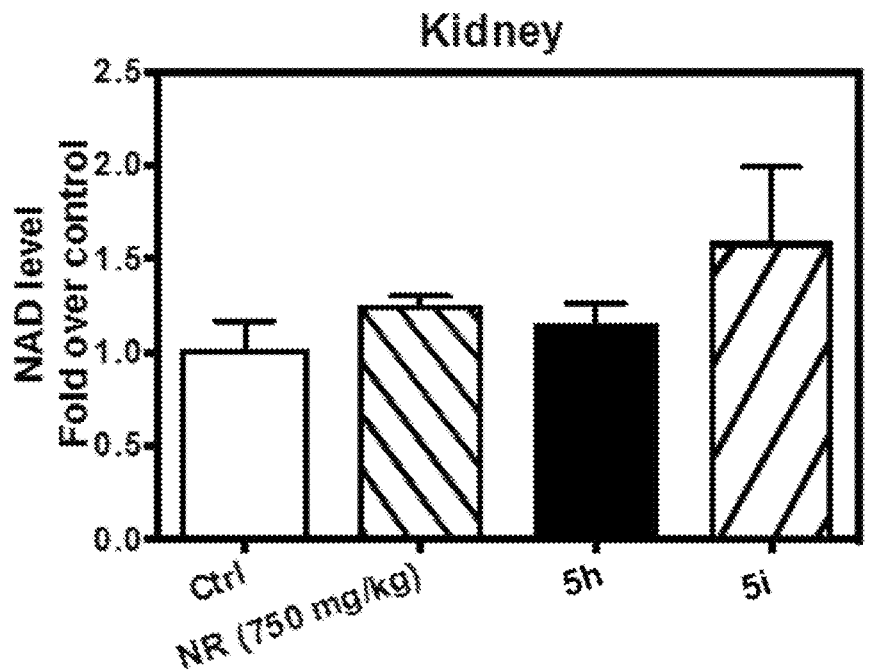
Figure 9C:
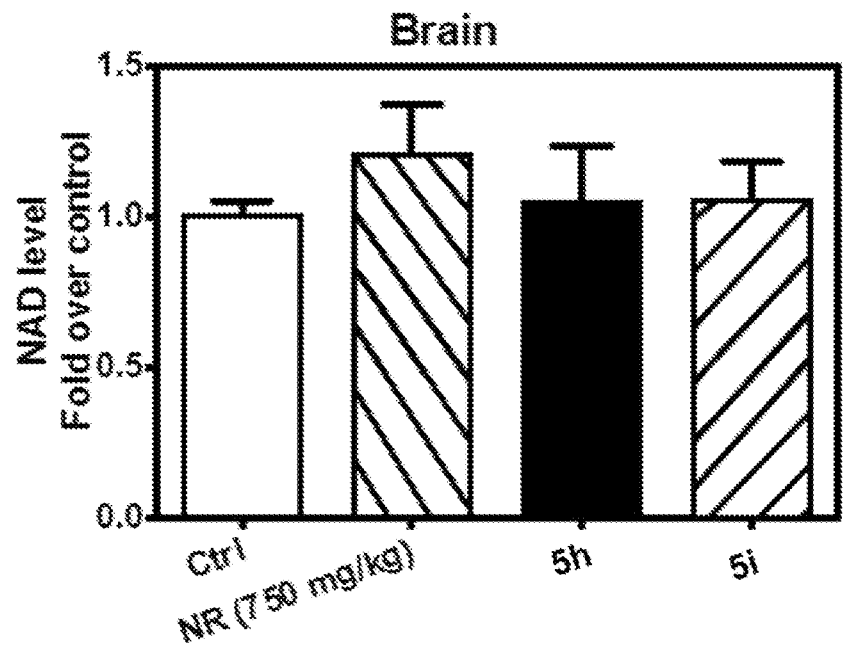
Figure 9D:
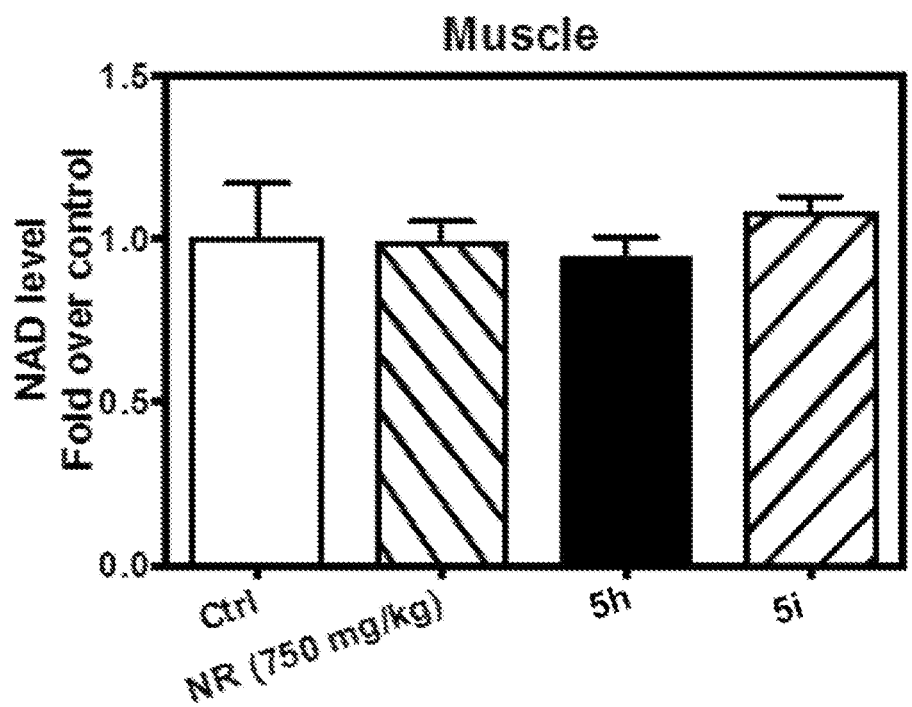
Figure 10A:
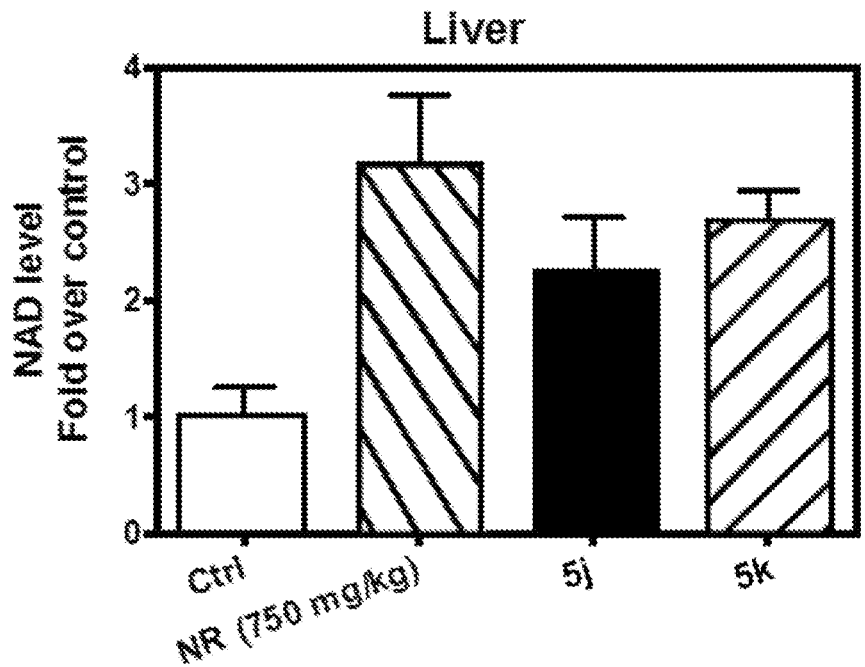
Figure 10B:
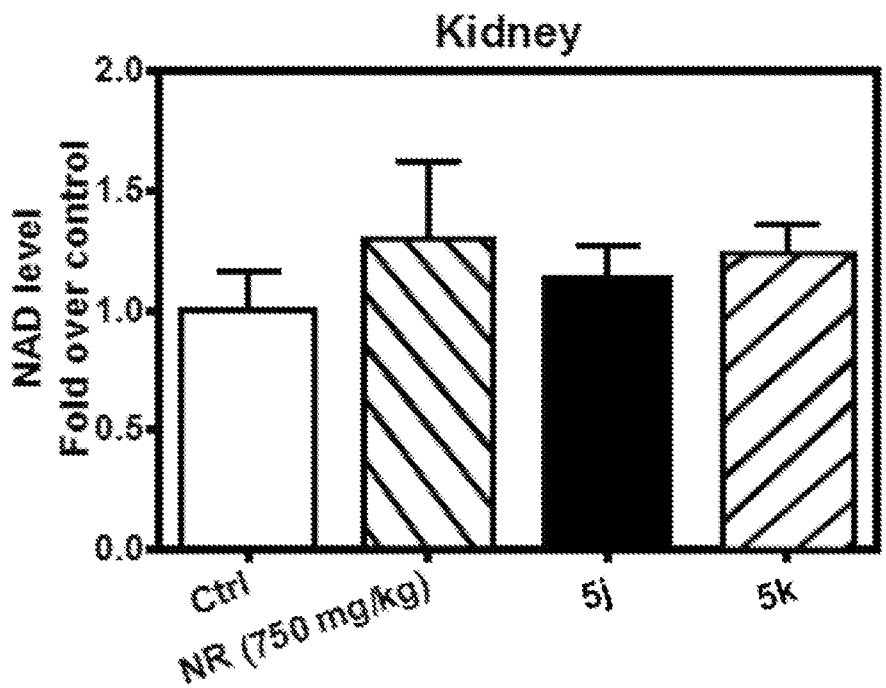
Figure 10C:
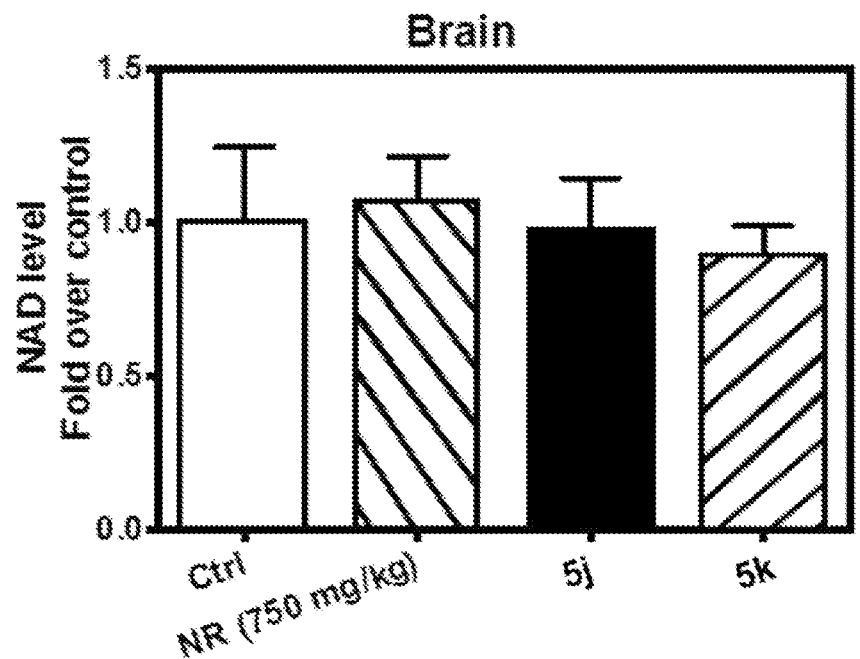
Figure 10D:
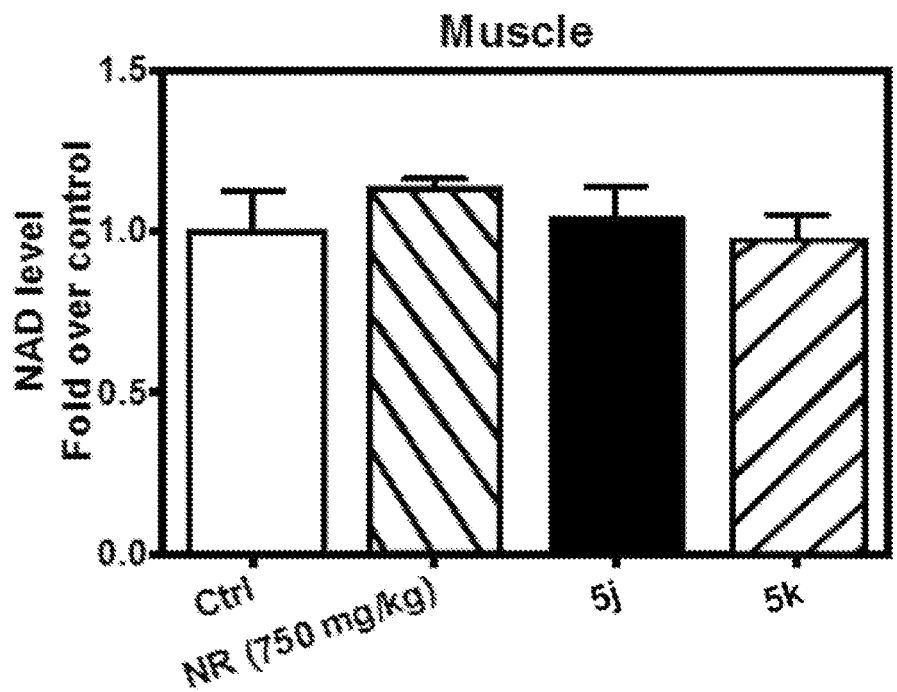

FIGS. 6A-6C show NAD+ blood levels in mice 1 h (FIG. 6A), 2 h (FIG. 6B), and 4 h (FIG. 6C), respectively, after administration of 500 mg/kg compound 5f, 500 mg/kg nicotinamide riboside, and control.

FIGS. 7A-7E show NAD+ levels in liver (FIG. 7A), kidney (FIG. 7B), brain (FIG. 7C), muscle (FIG. 7D), and heart (FIG. 7E), respectively, in mice 4 h after administration of 750 mg/kg compound 5d, 750 mg/kg compound 5c, 750 mg/kg nicotinamide riboside, and control.

FIGS. 8A-8D show NAD+ levels in liver (FIG. 8A), kidney (FIG. 8B), brain (FIG. 8C), and muscle (FIG. 8D), respectively, in mice 4 h after administration of 750 mg/kg compound 5a, 750 mg/kg compound 5g, 750 mg/kg nicotinamide riboside, and control.

FIGS. 9A-9D show NAD+ levels in liver (FIG. 9A), kidney (FIG. 9B), brain (FIG. 9C), and muscle (FIG. 9D), respectively, in mice 4 h after administration of 750 mg/kg compound 5h, 750 mg/kg compound 5i, 750 mg/kg nicotinamide riboside, and control.

FIGS. 10A-10D show NAD+ levels in liver (FIG. 10A), kidney (FIG. 10B), brain (FIG. 10C), and muscle (FIG. 10D), respectively, in mice 4 h after administration of 750 mg/kg compound 5j, 750 mg/kg compound 5k, 750 mg/kg nicotinamide riboside, and control.

DETAILED DESCRIPTION OF THE INVENTION

In an embodiment, the invention provides a process for the preparation of a compound of formula (I):

(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof, wherein the process comprises the step of:

reacting a compound of formula (III):

(III)

with a mixture of $POCl_3$ and $PO(OR^5)_3$, wherein $R^5$ is $C_1$-$C_6$ alkyl, followed by treatment with water to form the compound of formula (I).

In certain embodiments, R is straight chain $C_3$-$C_{20}$ alkyl. In certain preferred embodiments, R is n-propyl, n-butyl, n-pentyl, n-hexyl, n-heptyl, or n-octyl. In a particular embodiment, R is n-propyl.

In certain embodiments, R is branched chain $C_3$-$C_{20}$ alkyl. In certain preferred embodiments, R is 2,2-dimethylpropyl, 3-methylbutyl, isopropyl, 1,1-dimethylpropyl, or t-butyl.

In an embodiment, $R^5$ is ethyl.

In an embodiment, the compound of formula (III) is prepared by reacting a compound of formula (II):

(II)

wherein R' is methyl or ethyl, with a compound of formula ROH in the presence of a base in a solvent to form a compound of formula (III).

In an embodiment, the base is potassium t-butoxide.

In an embodiment, the solvent is ROH.

In certain of these embodiments, R is n-propyl, n-butyl, n-pentyl, n-hexyl, n-heptyl, or n-octyl.

In an embodiment, the solvent further comprises 2,2,2-trifluoroethanol.

In certain embodiments, the compound of formula (III) is prepared by reacting a nicotinate ester (IV):

(IV)

with 1,2,3,4-tetra-O-acetyl-D-ribofuranose to provide a compound of formula (V):

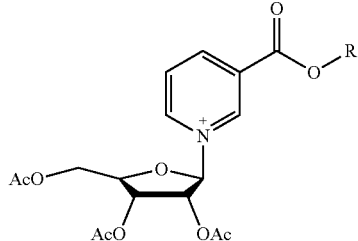
(V)

and reacting the compound of formula (V) with a base to form the compound of formula (III).

In certain of these embodiments, R is branched chain $C_3$-$C_{20}$ alkyl. In certain preferred embodiments, R is 2,2-dimethylpropyl, 3-methylbutyl, isopropyl, 1,1-dimethylpropyl, or t-butyl.

In an embodiment, the invention provides a process for the preparation of a compound of formula (I):

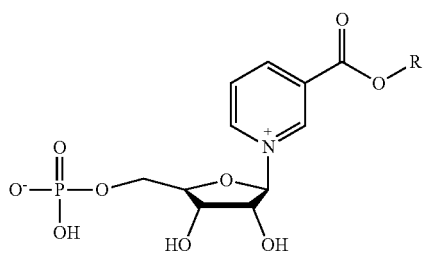
(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:

(i) reacting a compound of formula (II):

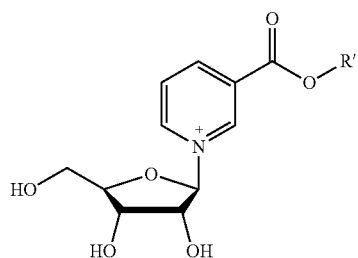
(II)

wherein R' is methyl or ethyl, with a compound of formula ROH in the presence of a base in a solvent to form a compound of formula (III):

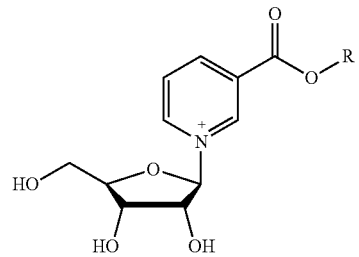
(III)

and (ii) reacting the compound of formula (III) with a mixture of $POCl_3$ and $PO(OR^5)_3$, wherein $R^5$ is $C_1$-$C_6$ alkyl, followed by treatment with water to form the compound of formula (I).

In certain embodiments, R is straight chain $C_3$-$C_{20}$ alkyl. In certain preferred embodiments, R is n-propyl, n-butyl, n-pentyl, n-hexyl, n-heptyl, or n-octyl.

In certain of these embodiments, $R^5$ is ethyl.

In certain preferred embodiments, the base is potassium t-butoxide.

In certain preferred embodiments, the solvent is ROH.

In certain embodiments, the solvent comprises 2,2,2-trifluoroethanol.

In another embodiment, the invention provides a process for the preparation of a compound of formula (I):

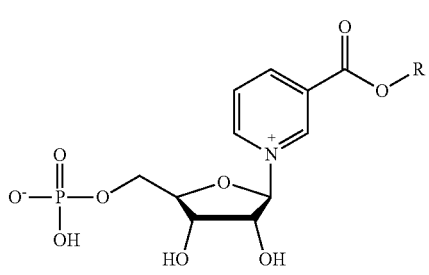
(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:

(i) reacting a nicotinate ester (IV):

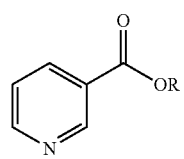
(IV)

with 1,2,3,4-tetra-O-acetyl-D-ribofuranose to provide a compound of formula (V):

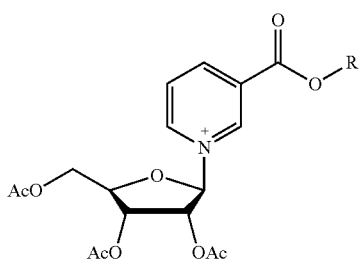

(ii) reacting the compound of formula (V) with a base to form the compound of formula (III):

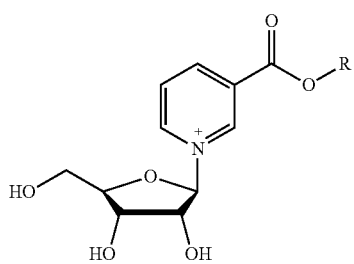

and (ii) reacting the compound of formula (III) with a mixture of POCl$_3$ and PO(OR$^5$)$_3$, wherein R$^5$ is C$_1$-C$_6$ alkyl, followed by treatment with water to form the compound of formula (I).

In certain embodiments, R is branched chain C$_3$-C$_{20}$ alkyl. In certain preferred embodiments, R is 2,2-dimethylpropyl, 3-methylbutyl, isopropyl, 1,1-dimethylpropyl, or t-butyl.

In an embodiment, the compound of formula (I) can be synthesized as shown in Scheme 1.

Scheme 1

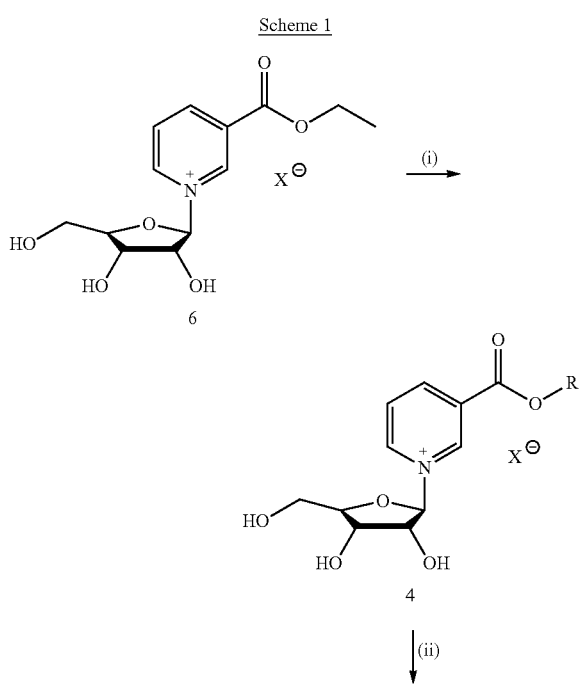

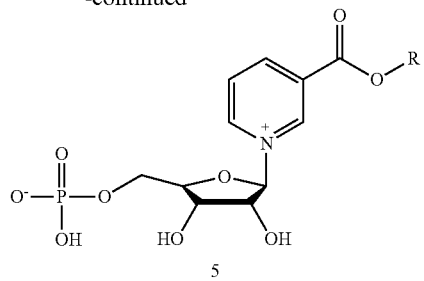

Reagents and conditions: (i) potassium tert-butoxide (2.0 eq), CF$_3$CH$_2$OH (2.0 eq) and corresponding alcohol, -20° C., 16 h, (ii) POCl$_3$ (2.5 eq), PO(OC$_2$H$_5$)$_3$, 0° C., 12 h.

Compound 6, wherein X$^-$ is an anion, is transesterified with an alcohol ROH in the presence of a base to provide compound 4 (i.e., a compound of formula (III)). The base can be any suitable base. For example, the base can be a salt of the alcohol ROH (e.g., a sodium, potassium, or cesium salt), sodium hydride, potassium hydride, a salt of an alcohol R"OH wherein R"OH is different from ROH, an organolithium compound, an organomagnesium compound, a tertiary amine (e.g., Hünig's base), an alkali or alkaline earth metal carbonate, and the like. In an embodiment, the base is potassium tert-butoxide. The base can be present in any suitable amount. In an embodiment, the base is present in an amount of 2.0 equivalents, based on the amount of compound 6.

The solvent can be any suitable solvent. For example, the solvent can be ROH (i.e., the same compound that participates in the reaction), tetrahydrofuran, dioxane, DMF, DMSO, and the like. In a preferred embodiment, the solvent is ROH.

In an embodiment, the solvent further comprises 2,2,2-trifluoroethanol. The 2,2,2-trifluoroethanol can be present in any suitable amount. In an embodiment, 2,2,2-trifluoroethanol is present at an amount of 2.0 equivalents based on the amount of compound 6.

It will be understood that, when a compound is shown as a cation without having an anion, the positive charge on the cation can be countered by any suitable anion or anionic component having a negative charge. The anion can be any suitable organic, inorganic, or polymeric anion without limitation. In an embodiment, the anion is trifluoromethanesulfonate.

Compound 4 can be phosphorylated using any suitable conditions. Preferably, compound 4 can be phosphorylated in a mixture of phosphorus oxychloride and PO(OR$^5$)$_3$, wherein R$^5$ is C$_1$-C$_6$ alkyl. Preferably, compound 4 is phosphorylated in a mixture of phosphorus oxychloride and triethylphosphate to provide compound 5 (i.e., a compound of formula (I)). The phosphorylation can be conducted at any suitable temperature. For example, the phosphorylation can be conducted at about -20° C. to about 50° C. and is preferably conducted at 0° C.

Compound 5 can be isolated using any suitable isolation technique. For example, compound 5 can be isolated by precipitation of compound 5 from an aqueous mixture or solution by the addition of a suitable solvent such as ethyl acetate, tetrahydrofuran, acetonitrile, and the like, followed by filtration to obtain compound 5 as a solid. Other isolation techniques, such as high performance liquid chromatography (HPLC) can also be used to isolate compound 5.

In an embodiment, the compound of formula (I) can be synthesized as shown in Scheme 2.

Scheme 2

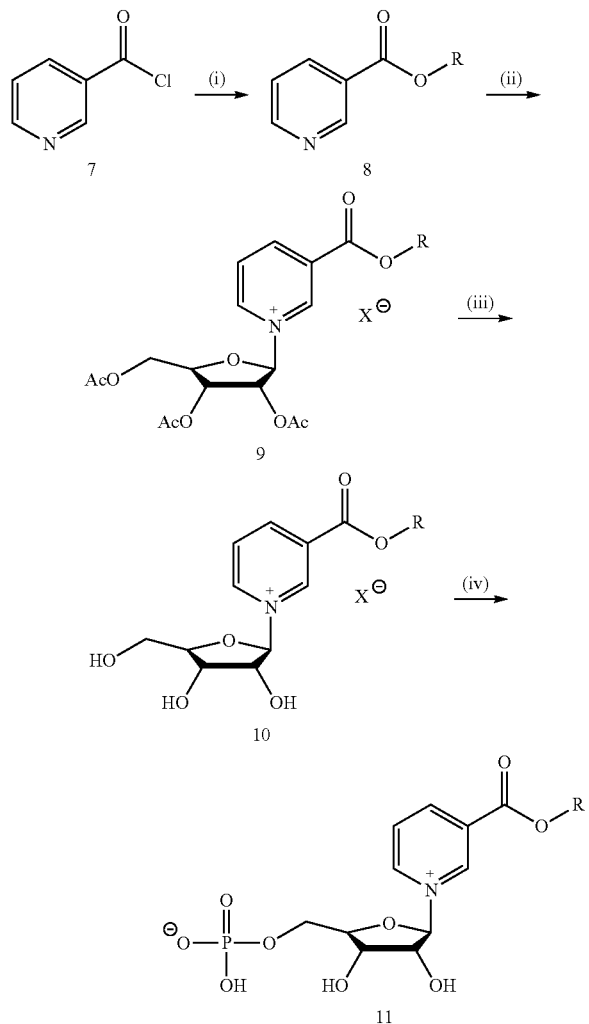

Reagents and conditions: (a): alcohols, triethylamine, 4-dimethylaminopyridine, DCM, -78° C. to reflux; (b): β-D-ribofuranose 1,2,3,5-tetraacetate, trimethylsilyl trifluoromethanesulfonate, DCM, reflux; (c): potassium tert-butoxide. THF, −78° C. to −20° C.; (d): phosphoryl chloride, triethyl phosphate Nicotinate ester 8 can be prepared using any suitable method. For example, nicotinoyl chloride 7 can be reacted with an alcohol ROH in the presence of a base such as trimethylamine and a basic catalyst such as 4-dimethylaminopyridine in a suitable solvent such as dichloromethane (DCM). Protected triacetyl nicotinate riboside 9 can be prepared by reacting nicotinate ester 9 with an acetylated riboside such as 1,2,3,5-tetra-O-acetyl-D-ribofuranose in the presence of a catalyst such as trimethylsilyl trifluoromethanesulfonate in a suitable solvent such as DCM to provide 9. Triacetyl nicotinate riboside 9 can be deprotected by reaction with a base such as potassium tert-butoxide in a solvent such as tetrahydrofuran (THF) to provide deprotected nicotinate riboside 10. Nicotinate riboside 10 can be phosphorylated as described herein to provide nucleotide 5.

In another embodiment, the invention provides a compound of formula (I):

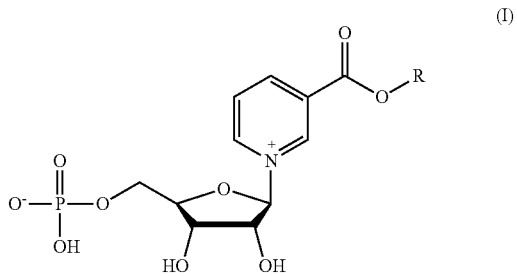

wherein R is straight or branched chain $C_3$-$C_{20}$ alkyl, straight or branched chain $C_2$-$C_{20}$ alkenyl, $C_2$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof.

In certain embodiments, R is straight chain $C_3$-$C_{20}$ alkyl. In certain preferred embodiments, R is n-propyl, n-butyl, n-pentyl, n-hexyl, n-heptyl, or n-octyl. In a particular embodiment, R is n-propyl and the compound has the structure:

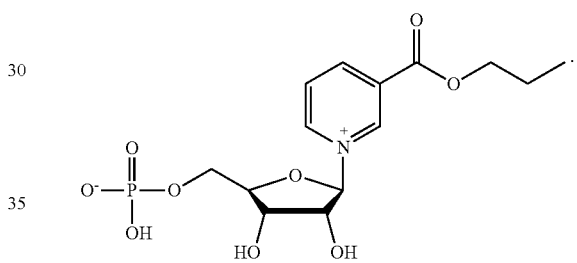

In certain embodiments, R is branched chain $C_3$-$C_{20}$ alkyl. In certain preferred embodiments, R is 2,2-dimethylpropyl, 3-methylbutyl, isopropyl, 1,1-dimethylpropyl, or t-butyl.

Referring now to terminology used generically herein, the term "alkyl" means a straight-chain or branched alkyl substituent containing from, for example, 3 to about 20 carbon atoms, e.g., from 3 to about 18 carbon atoms, from 3 to about 16 carbon atoms, from 3 to about 14 carbon atoms, from 3 to about 12 carbon atoms, from 3 to about 10 carbon atoms, from 3 to about 8 carbon atoms, or from 4 to 8 carbon atoms. The alkyl groups can be straight chain or branched. Examples of such substituents include propyl, isopropyl, n-butyl, sec-butyl, isobutyl, tert-butyl, pentyl, isoamyl, hexyl, and the like.

The term "alkenyl" refers to a group as described herein for alkyl wherein the alkenyl group contains 1 or more C=C double bonds. Examples of suitable alkenyl groups include 2-propen-1-yl, 2-buten-1-yl, 3-buten-1-yl, 2-penten-1-yl, 3-penten-1-yl, 4-penten-1-yl, 2-hexen-1-yl, 3-hexen-1-yl, 4-hexen-1-yl, 5-hexen-1-yl, and the like.

The term "alkynyl" refers to a group as described herein for alkyl wherein the alkynyl group contains 1 or more C≡C triple bonds. Examples of suitable alkynyl groups include 2-propyn-1-yl, 2-butyn-1-yl, 3-butyn-1-yl, 2-pentyn-1-yl, 3-pentyn-1-yl, 4-pentyn-1-yl, 2-hexyn-1-yl, 3-hexyn-1-yl, 4-hexyn-1-yl, 5-hexyn-1-yl, and the like.

The alkyl, alkenyl, or alkynyl groups may be unsubstituted or further substituted with hydroxyl groups, alkoxy groups, halo groups, and the like. The alkenyl or alkynyl groups may be straight chain or branched.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cycloalkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. Suitable bicyclic heterocyclyl groups include monocyclic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. The term "heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, pyridazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxy carbonyl, arylcarbonyl, aryloxy carbonyl, thio, alkylthio, arylthio, and the like, wherein the optional substituent can be present at any open position on the heterocyclyl or heteroaryl group, or with benzo groups, to form a group of, for example, benzofuran.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

Whenever a range of the number of atoms in a structure is indicated (e.g., a $C_3$-$C_{20}$, $C_3$-$C_{18}$, $C_3$-$C_{16}$, $C_3$-$C_{14}$, $C_3$-$C_{12}$, $C_3$-$C_5$, $C_3$-$C_6$, $C_3$-$C_4$, or $C_2$-$C_{12}$, $C_2$-$C_5$, $C_2$-$C_6$, $C_2$-$C_4$ alkenyl, alkynyl, etc.), it is specifically contemplated that any sub-range or individual number of carbon atoms falling within the indicated range also can be used. Thus, for instance, the recitation of a range of 3-20 carbon atoms (e.g., $C_3$-$C_{20}$), 3-18 carbon atoms (e.g., $C_3$-$C_{18}$), 3-16 carbon atoms (e.g., $C_3$-$C_{16}$), 3-14 carbon atoms (e.g., $C_3$-$C_{14}$), 3-12 carbon atoms (e.g., $C_3$-$C_{12}$), 3-10 carbon atoms (e.g., $C_3$-$C_{10}$), 3-8 carbon atoms (e.g., $C_3$-$C_8$), 3-6 carbon atoms (e.g., $C_3$-$C_6$), or 3-4 carbon atoms (e.g., $C_3$-$C_4$), 4-5 carbon atoms (e.g., $C_4$-$C_5$), 4-6 carbon atoms (e.g., $C_4$-$C_6$), 4-7 carbon atoms (e.g., $C_4$-$C_7$), 4-8 carbon atoms (e.g., $C_4$-$C_8$), 4-9 carbon atoms (e.g., $C_4$-$C_9$), 4-10 carbon atoms (e.g., $C_4$-$C_{10}$), 4-11 carbon atoms (e.g., $C_4$-$C_{11}$), 4-12 carbon atoms (e.g., $C_4$-$C_{12}$), 4-13 carbon atoms (e.g., $C_4$-$C_{13}$), 4-14 carbon atoms (e.g., $C_4$-$C_{14}$), 4-15 carbon atoms (e.g., $C_4$-$C_{15}$), 4-16 carbon atoms (e.g., $C_4$-$C_{16}$), 4-17 carbon atoms (e.g., $C_4$-$C_{17}$), 4-18 carbon atoms (e.g., $C_4$-$C_{18}$), 4-19 carbon atoms (e.g., $C_4$-$C_{19}$), and/or 4-20 carbon atoms (e.g., $C_4$-$C_{20}$), etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The phrase "salt" or "pharmaceutically acceptable salt" is intended to include nontoxic salts, which can be synthesized from the parent compound, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, a nonaqueous medium, such as ether, ethyl acetate, ethanol, isopropanol, or acetonitrile, is preferred. Lists of suitable salts are found in *Remington's Pharmaceutical Sciences,* 18th ed., Mack Publishing Company, Easton, Pa., 1990, p. 1445, and *Journal of Pharmaceutical Science,* 66: 2-19 (1977). For example, a suitable salt can be a salt of an alkali metal (e.g., sodium or potassium), alkaline earth metal (e.g., calcium), or salt of ammonium or alkylammonium, for example, monoalkylammonium, dialkylammonium, trialkylammonium, or tetraalkylammonium.

Examples of pharmaceutically acceptable salts for use in the inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic acids, for example, methanesulfonic, trifluoromethanesulfonic, benzenesulfonic, and p-toluenesulfonic acids.

The invention further provides a composition, preferably a pharmaceutical composition, comprising a compound as described above in any of the embodiments and a suitable carrier, preferably a pharmaceutically acceptable carrier. The invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the invention.

The pharmaceutically acceptable carrier can be any of those conventionally used and is limited only by chemico-physical considerations, such as solubility and lack of reactivity with the compound, and by the route of administration. In addition to the following described pharmaceutical compositions, the compounds of the invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. The pharmaceutically acceptable carrier preferably is chemically inert to the active compounds and has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the invention.

The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. The compounds of the invention also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the invention may be made into injectable formulations. The requirements for effective pharmaceutical carriers for injectable compositions are well known. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The invention also provides a nutraceutical composition comprising a compound of the invention. The term nutraceutical as used herein denotes the usefulness in both the nutritional and pharmaceutical field of application. The nutraceutical compositions according to the invention may be in any form that is suitable for administrating to the animal body including the human body, especially in any form that is conventional for oral administration, e.g. in solid form such as (additives/supplements for) food or feed, food or feed premix, tablets, pills, granules, dragees, capsules, and effervescent formulations such as powders and tablets, or in liquid form such as solutions, emulsions or suspensions as e.g. beverages, pastes and oily suspensions. Controlled (delayed) release formulations incorporating the compounds according to the invention also form part of the invention. Furthermore, a multi-vitamin and mineral supplement may be added to the nutraceutical compositions of the invention to obtain an adequate amount of an essential nutrient, which is missing in some diets. The multi-vitamin and mineral supplement may also be useful for disease prevention and protection against nutritional losses and deficiencies due to lifestyle patterns.

In an embodiment, the invention provides a method for increasing cell NAD$^+$ production comprising administering a compound of the invention or a salt thereof to a cell.

In certain embodiments, the cell is in a mammal having a lipid disorder, a metabolic dysfunction, a cardiovascular disease, CNS or PNS trauma, a neurodegenerative disease or condition, or hearing loss, or is in a mammal that has been exposed to a toxic agent. In certain embodiments, the cell is in a mammal at risk for hearing loss. In certain other embodiments, the cell is in a mammal, and the compound is administered in an amount effective for promoting the function of the metabolic system, promoting muscle function or recovery, promoting the function of the auditory system, or promoting cognitive function In another embodiment, the invention provides a method of improving mitochondrial density in a cell, wherein the method comprises administering to the cell a compound of the invention or a salt thereof. In certain embodiments, the cell is in a mammal having a lipid disorder, a metabolic dysfunction, a cardiovascular disease, CNS or PNS trauma, a neurodegenerative disease or condition, hearing loss, or is in a mammal that has been exposed to a toxic agent. In certain embodiments, the cell is in a mammal at risk for hearing loss. In certain other embodiments, the cell is in a mammal, and the compound is administered in an amount effective for promoting the function of the metabolic system, promoting muscle function or recovery, promoting the function of the auditory system, or promoting cognitive function.

Exemplars of the compounds of the invention exhibit a surprising and unexpected effect on mammalian tissues vis-a-vis NAD$^+$ increases. This effect occurs at doses of 100-1000 mg/kg where other compounds at any concentration are not efficacious to achieve the effect. Because of esterification, the compounds are also more lipophilic than their respective unesterified relatives, which may provide for increased absorption and blood-brain-barrier (BBB) penetration characteristics. Key features of the compounds are potency, ease of access, improved biological efficacy in enhancing NAD$^+$, and opportunities for improved drug behavior from enhanced lipophilicity.

In some embodiments, the invention provides a method for increasing mammalian cell NAD$^+$ production comprising administering a compound of the invention or a pharmaceutically acceptable salt thereof to a cell. Nicotinamide adenine dinucleotide (NAD or NAD$^+$) is important as a co-enzyme for different enzymes. Recent studies depicted that, being the co-substrate of SIR2 (silent information regulator 2), NAD$^+$ has a role in regulating multiple biological processes, such as p53 regulated apoptosis, fat storage, stress resistance, and gene silencing. Without limiting the potential uses of the compositions described herein by any single theory, there are various pathways through which nicotinamide riboside (NR), dihydronicotinamide riboside (NRH), nicotinic acid riboside (NAR), and dihydronicotinic acid riboside (NARH or NaR-H) as well as nicotinic acid mononucleotide (NaMN) and their derivatives are currently thought to be metabolized. NR is a known as NAD$^+$ precursors for both human and yeast. NR is able to enter a salvage pathway that leads to biological synthesis of NAD$^+$ under the action of the enzyme nicotinamide riboside kinase (Nrk). NR can be converted to nicotinamide mononucleotide (NMN) whereas nicotinic acid riboside (NaR) is converted to nicotinic acid mononucleotide (NAMN) by respective phosphorylations mediated by nicotinamide riboside kinases (Nrk). The mononucleotides are then converted to corresponding dinucleotides NAD$^+$ and nicotinic acid adenine dinucleotide (NaAD) by the enzyme nicotinamide mononucleotide adenylyltransferase (Nmnat). Alternatively, NR and NAR can enter NAD metabolism by means of other metabolic paths, which include action from enzymes that separate the nicotinamide or nicotinic acid moiety from the sugar. Such a path includes the action of phosphorylases that have been shown to degrade NR and NaR in cells to form nicotinamide and nicotinic acid respectively, and ribose-1-phosphate. Both nicotinamide and nicotinic acid are competent to enter NAD$^+$ metabolism and be converted to NAD+ by the action of the enzymes nicotinamide pyrophosphoribosyltransferase and nicotinic acid phosphoribosyltransferase respectively, to form NMN and NaMN respectively.

Downstream of NAD are other enzymes which mediate NAD effects. For example, sirtuins are class III histone deacetylases (HDACs) and also are ADP-ribosyl transferases. Sirtuins deacetylate lysine residues in a novel chemical reaction that consumes nicotinamide adenine dinucleotide (NAD$^+$), releasing nicotinamide, O-acetyl-ADPribose (AADPR), and the deacetylated substrate. By these activities, and by altering intracellular NAD$^+$ levels, one can improve the health of a cell, but introduction of compounds that enter NAD$^+$ metabolic pathways can also prove toxic to cells. In some embodiments, the invention relates to the use of compounds disclosed herein to manipulate NAD$^+$ levels, to modulate the activity of sirtuins and other ADP-ribosyl transferases, and to modulate inosine 5'-monophosphate dehydrogenase. These embodiments are used to destroy or weaken the defenses of cancer cells, or to promote survival of neurons, myocytes, or stem cells via addition to growth media.

Nicotinic acid is an effective agent in controlling low-density lipoprotein cholesterol, increasing high-density lipoprotein cholesterol, and reducing triglyceride and lipoprotein (a) levels in humans. Though nicotinic acid treatment affects all of the key lipids in the desirable direction and has been shown to reduce mortality in target populations, its use is limited because of a side effect of heat and redness termed flushing. Further, nicotinamide is neuroprotective in model systems, presumably due to multiple mechanisms including increasing mitochondrial NAD$^+$ levels.

In addition, NR and derivatives thereof have proved useful in model systems and in clinical trials in humans for a variety of uses, including promoting healthy aging, supporting and promoting healthy metabolic function, supporting and promoting cognitive function, neuroprotection in CNS and PNS trauma including stroke, and in neurogenerative diseases and conditions including essential tremor, Parkinson disease, Alzheimer disease, Huntington disease, ataxia, catatonia, epilepsy, neuroleptic malignant syndrome, dystonia, neuroacanthocytosis, Pelizaeus-Merzbacher, progressive supranuclear palsy, Striatonigral degeneration, Tardive dyskinesias, lysosomal storage disorders, including lipid storage disorders (including Gaucher's and Niemann-Pick diseases), gangliosidosis (including Tay-Sachs disease), leukodystrophies, mucopolysaccharidoses, glycoprotein storage disorders, and mucolipidoses. NR and derivatives thereof have been found useful to prevent hearing loss due to aging or exposure to loud sounds. NR and derivatives thereof can protect cells from damage to exposure to toxins, including damage to myocytes caused by statins. NR and derivatives thereof can slow or prevent the death of islet cells that produce insulin. NR and derivatives thereof have been found to increase the number of, and improve the function of, mitochondria.

NaMN derivatives may be bioavailable and are ultimately convertible by metabolism to nicotinic acid or nicotinic acid riboside (NAR), nicotinic acid mononucleotide (NaMN), Nicotinic acid adenine dinucleotide (NaAD) and ultimately to NAD+, thereby providing the benefits of the compounds as discussed above. Accordingly, one embodiment of the invention relates to the use of compositions comprising compounds disclosed herein that work through the nicotinamide riboside kinase pathway or other pathways of $NAD^+$ biosynthesis which have nutritional and/or therapeutic value in improving poor plasma lipid profiles in lipid disorders, (e.g., dyslipidemia, hypercholesterolaemia or hyperlipidemia), metabolic dysfunction in type I and II diabetes, cardiovascular disease, and other physical problems associated with obesity, protecting islet cells to treat or prevent development of diabetes, neuroprotection to treat trauma and neurodegenerative diseases and conditions, protecting muscle cells from toxicity and damage from workouts or trauma, promoting the function of the auditory system, treating or preventing hearing loss, and dietary supplement and food ingredient uses for promoting metabolic function, muscle function and healing/recovery, cognitive function, and mitochondrial function.

In some embodiments, the invention relates to the use of compounds disclosed herein as agonist and antagonist of enzymes in the pathway of $NAD^+$ biosynthesis. In further embodiments, the NaMN derivatives disclosed herein are agonists, i.e., stimulate activities normally stimulated by naturally occurring substances, of one or more sirtuins, preferably SIRT1 in humans or Sir2p in yeast. In further embodiments, the NaMN derivatives are antagonists of one or more of the sirtuins.

In some embodiments, the invention provides a method of improving metabolic function, including increased mitochondrial densities, insulin sensitivity, or exercise endurance in a mammal, wherein the method comprises administering to the mammal a compound of the invention or a pharmaceutically acceptable salt, or salt acceptable for dietary supplements or food ingredients, thereof. Under calorie restriction, cellular energy depletion causes rising AMP levels, and an increase in the $NAD^+$ level as compared to the reduced level (NADH) results in activation of AMPK. AMPK activation leads to PGC-1 alpha activation which leads to mitochondrial biosynthesis (Lopez-Lluch, et al., *Experimental Gerontology*, 43 (9): 813-819 (2009) [doi: 10.1016/j.exger.2008.06.014]). Increasing mitochondrial biosynthesis will lead to increased mitochondrial density in the muscle cells. Increased mitochondrial density will increase athletic performance in terms of muscle strength and endurance.

In some embodiments, the invention provides a method of treating or preventing a disease or condition in a mammal in need thereof, wherein the method comprises administering to the mammal a compound of the invention or a pharmaceutically acceptable salt thereof, wherein the disease or condition is CNS or PNS trauma, or a neurodegenerative disease or condition.

$NAD^+$ levels decrease in injured, diseased, or degenerating neural cells and preventing this $NAD^+$ decline efficiently protects neural cells from cell death. Araki & Milbrandt, *Science*, 305(5686): 1010-1013 (2004), and Wang et al., "A local mechanism mediates NAD-dependent protection of axon degeneration," *J. Cell Biol.*, 170(3): 349-55 (2005), hereby incorporated by reference. As a number of inventive compounds disclosed herein are capable of increasing intracellular levels of $NAD^+$, these compounds are useful as a therapeutic or nutritional supplement in managing injuries, diseases, and disorders effecting the central nervous system and the peripheral nervous system, including but not limited to trauma or injury to neural cells, diseases or conditions that harm neural cells, and neurodegenerative diseases or syndromes. Some neurodegenerative diseases, neurodegenerative syndromes, diseases, conditions that harm neural cells, and injury to neural cells are described above. The inventive compounds disclosed herein preferably are capable of passing the blood-brain-barrier (BBB).

In some embodiments, the invention provides a method of protecting a mammal from neurotrauma, wherein the method comprises administering to the mammal a compound of the invention or a pharmaceutically acceptable salt thereof. In certain of these embodiments, the neurotrauma results from blast injury or noise. In these embodiments, the agent increases intracellular $NAD^+$ in one or more cells selected from the group consisting of spiral ganglia nerve cells, hair cells, supporting cells, and Schwann cells.

In certain embodiments, the agent suppresses oxidative damage in the cell. In certain embodiments, the compound activates SIRT3. Endogenous SIRT3 is a soluble protein located in the mitochondrial matrix. Overexpression of SIRT3 in cultured cells increases respiration and decreases the production of reactive oxygen species. Without wishing to be bound by any particular theory, it is believed that activation of SIRT3 is implicated in suppression of oxidative damage in the aforesaid cells.

In certain embodiments, the treating of the mammal with the compound results in prevention of hearing loss. In other embodiments, the treating of the mammal with the agent results in the mitigation of hearing loss. The treating can be performed after exposure to the mammal to circumstances leading to hearing loss, such as exposure to noise, or can be performed prior to exposure of the mammal to the circumstances. The relationship of $NAD^+$ levels and protection from neurotrauma is disclosed in WO 2014/014828 A1, the contents of which are incorporated herein by reference. In certain embodiments, the compound supports the healthy structure or function of the auditory system in a mammal in need thereof.

Treating of the mammal with an effective amount of the compound, for example, in a dietary supplement or in a food ingredient composition, augments intracellular $NAD^+$ biosynthesis, wherein intracellular $NAD^+$ increases in spiral ganglia nerve cells, hair cells, supporting cells, Schwann cells, or a combination thereof. In some embodiments, the agent maintains axonal NAD+ levels following axonal injuries caused by acoustic trauma.

Statins, more mechanistically known as 3-hydroxy-3-methyglutaryl coenzyme A reductase inhibitors (or HMG-CoA inhibitors), are some of the world's most widely prescribed drugs. While statins are well tolerated at therapeutic doses, at higher doses and often in combination with other hypolipidaemic agents some potentially severe adverse effects have arisen. Most notably, cerivastatin (Baycol) was removed from the market in 2000 after 31 deaths in the United States from drug-associated rhabdomyolysis (breakdown of muscle fibers resulting in the release of muscle fiber contents into the circulation; some of these are toxic to the kidney) and associated acute renal failure in patients taking cerivastatin. Statins are also known to have severe interactions with fibric acid derivatives, especially with gemfibrozil. Of the 31 people who died taking cerivastatin, 12 were also taking gemfibrozil.

The most serious adverse effects of statins appear to occur in liver and muscle cells, although it could be predicted that because of their lipophilicity, cerebral effects might also be seen in some patients.

The exact mechanism of statin toxicities is unknown. The fact that toxicities are dose-dependent makes plausible the hypothesis that toxicities result from exaggeration of the drug's intended effect. In other words, cells die from lack of the downstream products of HMG-CoA.

HMG-CoA is the rate limiting enzyme in the mevalonate pathway, which, through three branches, leads to the synthesis of cholesterol, dolichol (the precursor to dolichol pyrophosphate, which is the first thing added to proteins in post-translational glycosylation), and to ubiquinone, also known as Coenzyme Q (found in the membranes of endoplasmic reticulum, peroxisomes, lysosomes, vesicles and notably the inner membrane of the mitochondrion where it is an important part of the electron transport chain; it is also has important antioxidant activities).

However, it is likely that depletion of CoQ leads to a breakdown in the electron transport chain, leading in turn to a buildup in NADH, and a depletion in $NAD^+$. Further, the reduced form of CoQ10, CoQ10H2, has an important cellular antioxidant function, which is to protect membranes and plasma lipoproteins against free radical-induced oxidation.

In some embodiments, the invention provides a method of reducing toxicity induced by a HMGCoA reductase inhibitor in a mammal, which method comprises administering to the mammal a therapeutically effective amount of a compound of the invention, wherein the mammal has been administered the HMGCoA reductase inhibitor in an amount that produces toxicity in the mammal in the absence of the administration of the compound of formula (I), and wherein the administration of the compound of claim 1 reduces the toxicity in the mammal. In some embodiments, the invention provides a method of reducing toxicity induced by a HMG-CoA reductase inhibitor in a mammal, which method comprises administering to the mammal a therapeutically effective amount of a compound of the invention and then administering to the mammal the HMGCoA reductase inhibitor in an amount that produces toxicity in the mammal in the absence of the administration of the compound of formula (I), whereby toxicity that would have been induced by the HMGCoA reductase inhibitor is reduced in the mammal by the administration of the compound of the invention. In some embodiments, the invention provides a method of reducing toxicity induced by a HMGCoA reductase inhibitor in a mammal, which method comprises administering to the mammal a therapeutically effective amount of a compound of the invention, whereby toxicity induced by the HMGCoA inhibitor is reduced in the mammal, wherein the compound of the invention is administered to the mammal following manifestation of toxicity by the mammal.

In some embodiments, the invention provides a method of reducing toxicity induced by a genotoxic agent in a mammal, which method comprises administering to the mammal a therapeutically effective amount of a compound of the invention, wherein the mammal has been administered the genotoxic agent in an amount that produces toxicity in the mammal in the absence of the administration of the compound of the invention, and wherein the administration of the compound reduces the toxicity in the mammal. The compound of the invention can be administered to the mammal prior to administration of the genotoxic or other toxic agent to the mammal, simultaneously with administration of the genotoxic or other toxic agent to the mammal, or after administration of the genotoxic or other toxic agent to the mammal, for example, after symptoms of toxicity resulting from administration of the genotoxic or other toxic agent appear in the mammal.

In some embodiments, the invention relates to the use of a compound of the invention to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (e.g., superoxide, peroxides, hydroxyl radicals). Repair systems in the cell excise and repair damage caused by toxins.

Enzymes that use $NAD^+$ play a part in the DNA repair process. Specifically, the poly(ADP-ribose) polymerases (PARPs), particularly PARP-1, are activated by DNA strand breaks and affect DNA repair. The PARPs consume $NAD^+$ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular $NAD^+$, leading to cellular necrosis. The apparent sensitivity of $NAD^+$ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of $NAD^+$ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that $NAD^+$ metabolism is an important player in cell stress response pathways. For example, upregulation of $NAD^+$ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated $NAD^+$ biosynthesis, which increases the available $NAD^+$ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Examples of cell and tissue protection linked to NAD+ and sirtuins include the finding that SIRT1 is required for neuroprotection associated with trauma and genotoxicity. SIRT1 can also decrease microglia-dependent toxicity of amyloid-beta through reduced NFKB signaling. SIRT1 and increased NAD+ concentrations provide neuroprotection in a model of Alzheimer's disease. Sirtuins are NAD+-dependent enzymes that have protein deacetylase and ADP-ribosyltransferase activities that upregulate stress response pathways. Evidence indicates that SIRT1 is upregulated by calorie restriction and in humans could provide cells with protection against apoptosis via downregulation of p53 and Ku70 functions. In addition, SIRT1 upregulates FOXO-dependent transcription of proteins involved in reactive oxygen species (ROS) detoxification, such as MnSOD. The sirtuin SIRT6 has been shown to participate in DNA repair pathways and to help maintain genome stability.

Pharmacological agents that target both NAD+ metabolism and sirtuins can provide tools to elucidate the involvement of these factors in modulating toxicity-induced tissue damage. Moreover, therapeutic options for treatment of acute and chronic tissue-degenerative conditions can emerge if sirtuins and NAD+ metabolism can be validated as providing enhanced tissue protection. Agents such as the plant polyphenols (e.g., resveratrol), the niacin vitamins, and the compound nicotinamide riboside can enhance cell survival outcomes by increasing NAD+ biosynthesis, reducing NAD+ depletion, and/or activating sirtuin enzymes.

PREFERRED EMBODIMENTS

The invention includes the following embodiments:

1. A process for the preparation of a compound of formula (I):

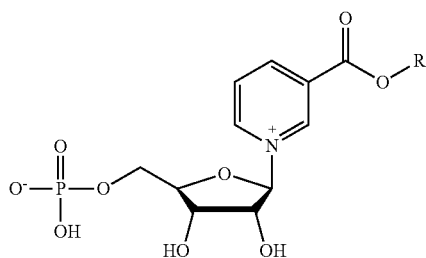

(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof, wherein the process comprises the step of reacting a compound of formula (III):

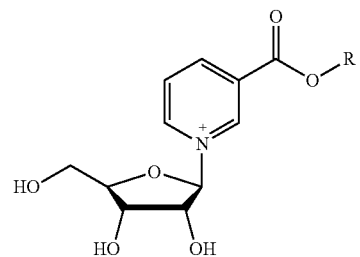

(III)

with a mixture of $POCl_3$ and $PO(OR^5)_3$, wherein $R^5$ is $C_1$-$C_6$ alkyl, followed by treatment with water to form the compound of formula (I).

2. The process of embodiment 1, wherein R is straight chain $C_3$-$C_{20}$ alkyl, straight chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl 3. The process of embodiment 1 or 2, wherein R is straight chain $C_3$-$C_{20}$ alkyl.

4. The process of any one of embodiments 1-3, wherein R is n-propyl, n-butyl, n-pentyl, n-hexyl, n-heptyl, or n-octyl.

5. The process of embodiment 1, wherein R is branched chain $C_3$-$C_{20}$ alkyl.

6. The process of embodiment 1, wherein R is 2,2-dimethylpropyl, 3-methylbutyl, isopropyl, 1,1-dimethylpropyl, or t-butyl.

7. The process of any one of embodiments 1-6, wherein $R^5$ is ethyl.

8. The process of embodiment 1 or 2, wherein the compound of formula (III) is prepared by reacting a compound of formula (II):

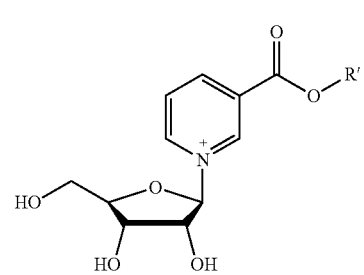

(II)

wherein R' is methyl or ethyl, with a compound of formula ROH in the presence of a base in a solvent to form the compound of formula (III).

9. The process of embodiment 8, wherein the base is potassium t-butoxide.

10. The process of embodiment 8 or 9, wherein the solvent is ROH.

11. The process of any one of embodiments 8-10, wherein R is straight chain $C_3$-$C_{20}$ alkyl.

12. The process of any one of embodiments 8-11, wherein R is n-propyl, n-butyl, n-pentyl, n-hexyl, n-heptyl, or n-octyl.

13. The process of any one of embodiments 8-12, wherein the solvent further comprises 2,2,2-trifluoroethanol.

14. The process of embodiment 1, wherein the compound of formula (III) is prepared by reacting a nicotinate ester (IV):

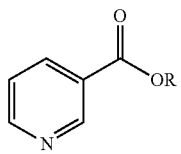

(IV)

with 1,2,3,4-tetra-O-acetyl-D-ribofuranose to provide a compound of formula (V):

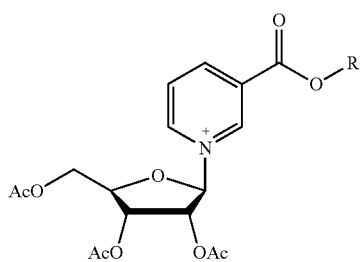

(V)

and reacting the compound of formula (V) with a base to form the compound of formula (III).

15. The process of embodiment 14, wherein R is branched chain $C_3$-$C_{20}$ alkyl.

16. The process of embodiment 14 or 15, wherein R is 2,2-dimethylpropyl, 3-methylbutyl, isopropyl, 1,1-dimethylpropyl, or t-butyl.

17. A process for the preparation of a compound of formula (I):

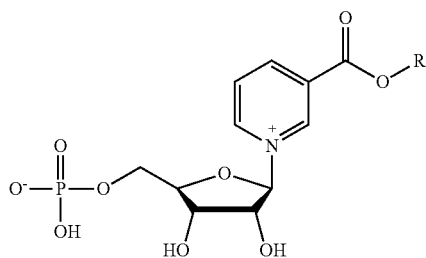

(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:

(i) reacting a compound of formula (II):

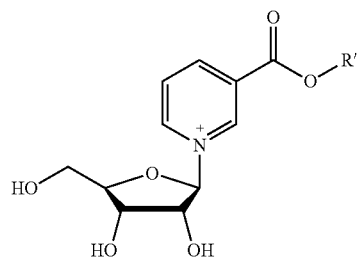

(II)

wherein R' is methyl or ethyl, with a compound of formula ROH in the presence of a base in a solvent to form a compound of formula (III):

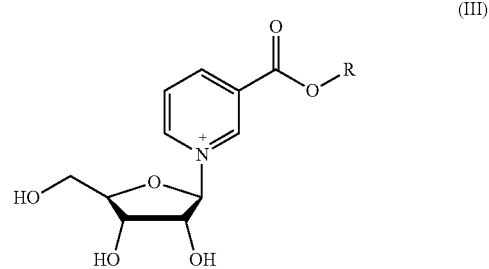

(III)

and (ii) reacting the compound of formula (III) with a mixture of $POCl_3$ and $PO(OR^5)_3$, wherein $R^5$ is $C_1$-$C_6$ alkyl, followed by treatment with water to form the compound of formula (I).

18. The process of embodiment, 17, wherein R is straight chain $C_3$-$C_{20}$ alkyl, straight chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl.

19. The process of embodiment 17, wherein R is straight chain $C_3$-$C_{20}$ alkyl.

20. The process of embodiment 17 or 18, wherein R is n-propyl, n-butyl, n-pentyl, n-hexyl, n-heptyl, or n-octyl.

21. The process of any one of embodiments 17-20, wherein $R^5$ is ethyl.

22. The process of any one of embodiments 17-21, wherein the base is potassium t-butoxide.

23. The process of any one of embodiments 17-22, wherein the solvent is ROH.

24. The process of any one of embodiments 17-23, wherein the solvent comprises 2,2,2-trifluoroethanol.

25. A process for the preparation of a compound of formula (I):

(I)

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl or $C_5$-$C_{10}$ heteroaryl, or a salt thereof, wherein the process comprises the steps of:

(i) reacting a nicotinate ester (IV):

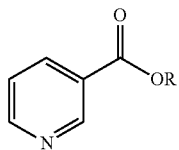

(IV)

with 1,2,3,4-tetra-O-acetyl-D-ribofuranose to provide a compound of formula (V):

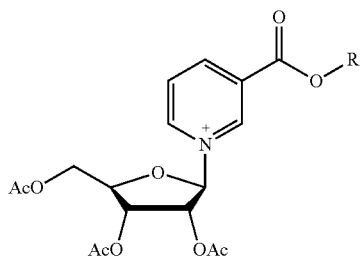

(V)

(ii) reacting the compound of formula (V) with a base to form the compound of formula (III):

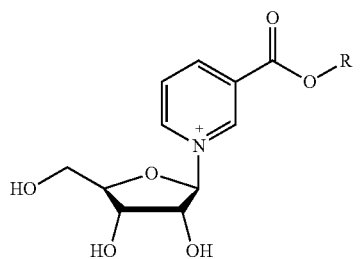

(III)

and
(iii) reacting the compound of formula (III) with a mixture of $POCl_3$ and $PO(OR^5)_3$, wherein $R^5$ is $C_1$-$C_6$ alkyl, followed by treatment with water to form the compound of formula (I).

26. The process of embodiment 25, wherein R is branched chain $C_3$-$C_{20}$ alkyl.

27. The process of embodiment 25 or 26, wherein R is 2,2-dimethylpropyl, 3-methylbutyl, isopropyl, 1,1-dimethylpropyl, or t-butyl.

28. A compound of formula (I):

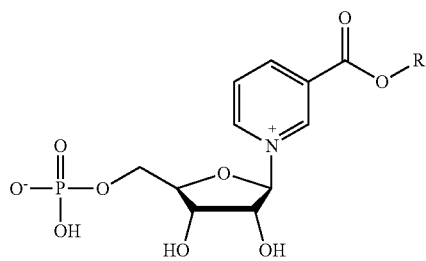

(I)

wherein R is straight or branched chain $C_3$-$C_{20}$ alkyl, straight or branched chain $C_2$-$C_{20}$ alkenyl, $C_2$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof.

29. The compound of embodiment 28, wherein R is straight chain $C_3$-$C_{20}$ alkyl, straight chain $C_2$-$C_{20}$ alkenyl, $C_2$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl 30. The compound or salt of embodiment 28 or 29, wherein R is straight chain $C_3$-$C_{20}$ alkyl.

31. The compound or salt of any one of embodiments 28-30, wherein R is n-propyl, n-butyl, n-pentyl, n-hexyl, n-heptyl, or n-octyl.

32. The compound or salt of embodiment 28, wherein R is branched chain $C_3$-$C_{20}$ alkyl.

33. The compound or salt of embodiment 28 or 32, wherein R is 2,2-dimethylpropyl, 3-methylbutyl, isopropyl, 1,1-dimethylpropyl, or t-butyl.

34. A pharmaceutical composition comprising the compound or salt of any one of embodiments 28-33 and a pharmaceutically acceptable carrier.

35. A nutraceutical composition comprising a compound or salt of any one of embodiments 28-33.

36. A method for increasing cell NAD+ production comprising administering to a cell a compound of any one of embodiments 28-33 or a salt thereof.

37. The method of embodiment 36, wherein the cell is in a mammal having a lipid disorder, a metabolic dysfunction, a cardiovascular disease, CNS or PNS trauma, a neurodegenerative disease or condition, or hearing loss, or is in a mammal that has been exposed to a toxic agent.

38. The method of embodiment 3236 wherein the cell is in a mammal at risk for hearing loss.

39. The method of embodiment 36, wherein the cell is in a mammal, wherein the compound is administered in an amount effective for promoting the function of the metabolic system, promoting muscle function or recovery, promoting the function of the auditory system, or promoting cognitive function.

40. A method of improving mitochondrial densities in a cell, wherein the method comprises administering to the cell a compound of any one of embodiments 28-33 or a salt thereof.

41. The method of embodiment 40, wherein the cell is in a mammal having a lipid disorder, a metabolic dysfunction, a cardiovascular disease, CNS or PNS trauma, a neurodegenerative disease or condition, hearing loss, or is in a mammal that has been exposed to a toxic agent.

42. The method of embodiment 40, wherein the cell is in a mammal at risk for hearing loss.

43. The method of embodiment 40, wherein the cell is in a mammal, wherein the compound is administered in an amount effective for promoting the function of the metabolic system, promoting muscle function or recovery, promoting the function of the auditory system, or promoting cognitive function.

EXAMPLES

The following examples further illustrate the invention but, of course, should not be construed as in any way limiting its scope.

Example 1

This example demonstrates a general synthesis of alkyl β-nicotinic ribosides.

Methyl β-nicotinic riboside and ethyl β-nicotinic riboside were synthesized as described in U.S. Pat. No. 8,106,184, the disclosure of which is incorporated herein by reference.

A solution of methyl β-nicotinic riboside or ethyl β-nicotinic riboside in a $C_3$-$C_{20}$ alky alcohol, $C_2$-$C_{20}$ alkenyl alcohol, $C_2$-$C_{20}$ alkynyl alcohol, $C_3$-$C_{20}$ cycloalkyl alcohol, $C_6$-$C_{10}$ aryl alcohol, $C_3$-$C_{20}$ heterocyclyl alcohol or $C_5$-$C_{10}$ heteroaryl alcohol is treated with 1.5-2.0 eq. of 2,2,2-trifluoroethanol and 1.5-2.0 eq. of potassium tert-butoxide at −20° C. for 16 h to provide the corresponding alkyl β-nicotinic riboside.

Example 2

This example demonstrates a synthesis of ((2R,3R,4S, 5R)-3,4-dihydroxy-5-(3-(propoxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(propoxycarbonyl)pyridin-1-ium trifluoromethanesulfonate 4a (100 mg, 0.30 mm) and triethyl phosphate (2 ml) were placed in a flame-dried round-bottom flask. The mixture was cooled to 0° C., and $POCl_3$ (70 μl, 0.75 mmol, 2.5 eq) was added dropwise to the mixture. The reaction mixture was stirred at the same temperature for 16 h. After completion, the reaction mixture was neutralized with cold saturated $NaHCO_3$ solution (pH=7). The resulting solution was directly concentrated under reduced pressure to minimum volume, and 2 ml of ethyl acetate was added thereto. Filtration afforded pure compound 5a (75 mg, yield 70%) as a white solid. $^1H$ NMR (500 MHz, $D_2O$): δ 9.51 (s, 2H), 9.13 (d, J=7.6 Hz, 1H), 8.36 (t, J=7.5, 14.5 Hz, 1H), 6.23 (d, J=5.4 Hz, 1H), 4.64-4.59 (m, 2H), 4.48-4.42 (m, 3H), 4.24 (m, 1H), 4.11 (m, 1H), 1.89-1.80 (m, 2H), 1.10 (t, J=7.5, 14.9 Hz, 3H); $^{13}C$ NMR (125 MHz, $D_2O$): δ 147.2, 143.3, 129.0, 100.4, 87.9, 77.7, 71.0, 69.3, 21.3, 9.6; $^{31}P$ NMR (500 MHz, $D_2O$): δ 2.34; LC-MS m/z $[M+H]^+$ calculated for $C_{14}H_{20}NO_9P$: 377.1; found 378.0. HRMS (ESI) m/z $[M+H]^+$ calculated for $C_{14}H_{21}NO_9P$ 378.0954, found 378.0943.

Example 3

This example demonstrates a synthesis of ((2R,3R,4S, 5R)-3,4-dihydroxy-5-(3-(butoxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(butoxycarbonyl)pyridin-1-ium trifluoromethanesulfonate 4b (300 mg, 0.864 mm) and triethyl phosphate (6 ml) were placed in a flame-dried round-bottom flask. The mixture was cooled to 0° C., and $POCl_3$ (202 μl, 2.3 mmol, 2.5 eq) was added dropwise to the mixture. The reaction mixture was stirred at the same temperature for 16 h. After completion, the reaction mixture was neutralized with cold saturated $NaHCO_3$ solution (pH=7). The resulting solution was directly concentrated under reduced pressure to minimum volume, and 6 ml of ethyl acetate was added thereto. Filtration afforded pure compound 5b (320 mg, yield 95%) as a white solid. $^1H$ NMR (500 MHz, $D_2O$): δ 9.40 (s, 1H), 9.31 (d, J=6.2 Hz, 1H), 9.06 (d, J=8.2 Hz, 1H), 8.27 (t, J=7.1, 14.3 Hz, 1H), 6.18 (d, J=5.3 Hz, 1H), 4.59 (m, 1H), 4.51 (t, J=5.2, 10.4 Hz, 1H), 4.43 (t, J=6.4, 12.7 Hz, 2H), 4.40-4.37 (m, 1H), 4.27-4.21 (m, 1H), 4.13-4.07 (m, 1H), 1.79-1.70 (m, 2H), 1.45-1.35 (m, 2H), 0.89 (t, J=8.2, 16.4 Hz, 3H); $^{13}C$ NMR (125 MHz, $D_2O$): δ 147.3, 128.7, 100.0, 77.7, 70.9, 67.7, 29.8, 18.6, 13.0; $^{31}P$ NMR (500 MHz, $D_2O$): δ 1.30; LC-MS m/z $[M+H]^+$ calculated for $C_{15}H_{22}NO_9P$: 391.1; found 392.0. HRMS (ESI) m/z $[M+H]^+$ calculated for $C_{15}H_{23}NO_9P$: 392.3110, found 392.1103.

Example 4

This example demonstrates a synthesis of ((2R,3R,4S, 5R)-3,4-dihydroxy-5-(3-(pentyloxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(pentyloxycarbonyl)pyridin-1-ium trifluoromethanesulfonate 4c (361 mg, 1.0 mm) and triethyl phosphate (6 ml) were placed in a flame-dried round-bottom flask. The mixture was cooled to 0° C., and $POCl_3$ (233 μl, 2.5 mmol, 2.5 eq) was added dropwise to the mixture. The reaction mixture was stirred at same temperature 16 h. After completion, the reaction mixture was neutralized with cold saturated $NaHCO_3$ solution (pH=7). The resulting solution was directly concentrated under reduced pressure to minimum volume, and 6 ml of ethyl acetate was added thereto. Filtration afforded pure compound 5c (400 mg, yield 98%) as a white solid. $^1H$ NMR (500 MHz, $D_2O$): δ 9.46 (s, 1H), 9.39 (d, J=6.9 Hz, 1H), 9.06 (d, J=1.9 Hz, 1H), 8.28 (t, J=6.5, 14.1 Hz, 1H), 6.18 (d, J=4.9 Hz, 1H), 4.6-4.51 (m, 2H), 4.45-4.35 (m, 3H), 4.23-4.17 (m, 1H), 4.09-4.04 (m, 1H), 1.80-1.74 (m, 2H), 1.41-1.24 (m, 4H), 0.83 (t, J=7.5, 14.6 Hz, 3H); $^{13}C$ NMR (125 MHz, $D_2O$): δ 162.9, 147.2, 143.0, 142.0, 130.8, 128.8, 100.1, 87.4, 77.6, 70.8, 67.9, 63.8, 62.2, 27.4, 21.7, 13.3; $^{31}P$ NMR (500 MHz, $D_2O$): δ 2.35; LC-MS m/z $[M+H]^+$ calculated for $C_{16}H_{24}NO_9P$: 405.1; found 406.1. HRMS (ESI) m/z $[M+H]^+$ calculated for $C_{16}H_{25}NO_9P$: 406.1267, found 406.1251.

Example 5

This example demonstrates a synthesis of ((2R,3R,4S, 5R)-3,4-dihydroxy-5-(3-(hexyloxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(hexyloxycarbonyl)pyridin-1-ium trifluoromethanesulfonate 4d (375 mg, 1.0 mm) and triethyl phosphate (6 ml) were placed in a flame dried round bottom flask. The mixture was cooled to 0° C. and $POCl_3$ (233 μl, 2.5 mmol, 2.5 eq) was added dropwise to the mixture. The reaction mixture was stirred at the same temperature for 16 h. After completion, the reaction was neutralized with cold saturated $NaHCO_3$ solution (pH=7). The resulting solution was directly concentrated under reduced pressure to minimum volume, and 6 ml of ethyl acetate was added thereto. Filtration afforded pure compound 5d (480 mg, yield 98%) as a white solid. $^1H$ NMR (500 MHz, $D_2O$): δ 9.44 (s, 1H), 9.30 (d, J=6.0 Hz, 1H), 9.03 (d, J=7.5 Hz, 1H), 8.23 (t, J=7.3, 14.2 Hz, 1H), 6.15 (d, J=5.4 Hz, 1H), 4.58-4.53 (m, 1H), 4.48 (t, J=4.9, 10.0 Hz, 2H), 4.43-4.33 (m, 4H), 4.25-4.18 (m, 1H), 4.10-4.04 (m, 1H), 1.77-1.70 (m, 2H), 1.40-1.31 (m, 2H), 1.29-1.19 (m, 2H), 0.78 (t, J=7.0, 14.0 Hz, 3H); $^{13}C$ NMR (125 MHz, $D_2O$): δ 147.2, 142.8, 141.8, 130.9, 128.6, 99.9, 87.2, 77.7, 70.8, 67.9, 64.1, 30.6, 27.6, 24.8, 21.9, 13.3; $^{31}P$ NMR (500 MHz, $D_2O$): δ 1.24; LC-MS m/z $[M+H]^+$ calculated for $C_{17}H_{26}NO_9P$: 419.1; found 420.1. HRMS (ESI) m/z $[M+H]^+$ calculated for $C_{17}H_{27}NO_9P$, 420.1423, found 420.1410.

Example 6

This example demonstrates a synthesis of ((2R,3R,4S, 5R)-3,4-dihydroxy-5-(3-(heptyloxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(heptyloxycarbonyl)pyridin-1-ium trifluoromethanesulfonate 4e (389 mg, 1.0 mm) and triethyl phosphate (6 ml) were placed in a flame-dried round-bottom flask. The mixture was cooled to 0° C., and POCl$_3$ (233 μl, 2.5 mmol, 2.5 eq) was added dropwise to the mixture. The reaction mixture was stirred at the same temperature for 16 h. After completion, the reaction mixture was neutralized with cold saturated NaHCO$_3$ solution (pH=7). The resulting solution was directly concentrated under reduced pressure to minimum volume, and 6 ml of ethyl acetate was added thereto. Filtration afforded pure compound 5e (500 mg, yield 98%) as a white solid. $^1$H NMR (500 MHz, D$_2$O): δ 9.41 (s, 1H), 9.26 (d, J=6.4 Hz, 1H), 9.00 (d, J=8.0 Hz, 1H), 8.21 (t, J=7.4, 14.6 Hz, 1H), 6.14 (d, J=5.3 Hz, 1H), 4.53-4.50 (m, 2H), 4.45 (t, J=5.3, 10.2 Hz, 1H), 4.39-4.30 (m, 4H), 4.22-4.15 (m, 1H), 4.07-4.00 (m, 1H), 1.79-1.66 (m, 2H), 1.36-1.28 (m, 2H), 1.27-1.20 (m, 2H), 1.19-1.13 (m, 2H), 0.73 (t, J=7.2, 14.1 Hz, 3H); $^{13}$C NMR (125 MHz, D$_2$O): δ 162.9, 147.2, 142.9, 141.9, 130.9, 128.7, 99.9, 87.3, 77.6, 70.8, 67.9, 64.1, 31.0, 28.0, 27.6, 25.1, 22.0, 13.4; $^{31}$P NMR (500 MHz, D$_2$O): δ 1.33; LC-MS m/z [M+H]$^+$ calculated for C$_{18}$H$_{28}$NO$_9$P: 433.2; found 434.1. HRMS (ESI) m/z [M+H]$^+$ calculated for C$_{18}$H$_{29}$NO$_9$NaP: 456.1399, found 456.1385.

Example 7

This example demonstrates a synthesis of ((2R,3R,4S,5R)-3,4-dihydroxy-5-(3-(octyloxycarbonyl)pyridin-1-ium-1-yl)tetrahydrofuran-2-yl)methyl hydrogen phosphate.

1-((2R,3S,4R,5R)-3,4-dihydroxy-5-(hydroxymethyl)tetrahydrofuran-2-yl)-3-(octyloxycarbonyl)pyridin-1-ium trifluoromethanesulfonate 4f (403 mg, 1.0 mm) and triethyl phosphate (6 ml) were placed in a flame-dried round-bottom flask. The mixture was cooled to 0° C., and POCl$_3$ (233 μl, 2.5 mmol, 2.5 eq) was added dropwise to the mixture. The reaction mixture was stirred at the same temperature for 16 h. After completion, the reaction mixture was neutralized with cold saturated NaHCO$_3$ solution (pH=7). The resulting solution was directly concentrated under reduced pressure to minimum volume, and 6 ml of ethyl acetate was added thereto. Filtration afforded pure compound 5f (520 mg, yield 98%) as a white solid. $^1$H NMR (500 MHz, D$_2$O): δ 9.48 (s, 1H), 9.34 (d, J=6.0 Hz, 1H), 9.07 (d, J=6.0 Hz, 1H), 8.29 (t, J=6.2, 14.6 Hz, 1H), 6.20 (d, J=5.3 Hz, 1H), 4.53-4.50 (m, 2H), 4.60 (s, 1H), 4.54-4.50 (m, 1H), 4.46-4.37 (s, 2H), 4.28-4.21 (m, 1H), 4.15-4.07 (m, 1H), 1.81-1.73 (m, 2H), 1.44-1.17 (m, 9H), 0.75 (t, J=7.2, 14.1 Hz, 3H); $^{13}$C NMR (125 MHz, D$_2$O): δ 162.9, 147.3, 143.0, 141.9, 131.0, 128.9, 100.1, 87.4, 77.8, 70.9, 67.9, 64.2, 31.2, 28.5, 27.7, 25.2, 22.1, 13.5; $^{31}$P NMR (500 MHz, D$_2$O): δ 1.60; LC-MS m/z [M+H]$^+$ calculated for C$_{19}$H$_{29}$NO$_9$P: 447.2; found 448.1. HRMS (ESI) in z [M+H]$^+$ calculated for C$_{19}$H$_{30}$NO$_9$NaP: 470.1556, found 470.1544.

Example 8

This example demonstrates a general synthesis of secondary or tertiary alkyl nicotinate riboside derivatives.

General procedure for the synthesis of secondary or tertiary nicotinate esters. To a suspension of nicotinoyl chloride hydrochloride (1 mmol) and alcohol (1.0 mmol) in DCM at −78° C. was added trimethylamine (3.0 mmol) and 4-dimethylaminopyridine (0.1 mmol). The reaction mixture was refluxed for 4 hr and then poured onto saturated NaHCO$_3$ solution. The organic layer was collected and dried to provide an oily residue, which was subjected to chromatography and eluted with hexanes-ethyl acetate (10:0 to 10:1) to give the nicotinate ester (yields: 36-74%).

General procedure for the synthesis of triacetyl protected nicotinate ribosides. To the solution of nicotinate ester (0.55 mmol) and 1,2,3,5-tetra-O-acetyl-D-ribofuranose (0.5 mmol) in DCM was added trimethylsilyl trifluoromethanesulfonate (0.5 mmol) under argon. The reaction mixture was refluxed for 4 hr and volatiles were removed under reduced pressure to give an oily residue. The resulting oily residue was partitioned between hexanes-methanol (1:1) and the methanol layer was collected. Methanol was removed under reduced pressure to give the crude triacetyl protected nicotinate ribosides, which was used directly for next step without purification.

General procedure for acetyl deprotection. To the solution of triacetyl protected nicotinate ribosides (0.3 mmol) in THF was added potassium tert-butyloxide (3.0 mmol) in portions at −78° C. under argon. The reaction mixture was stirred for 4 hr at −78° C. Acetic acid (6.0 mmol) was then added to quench the reaction and volatiles were removed under reduced pressure to give the crude product, which was subjected to chromatography and eluted with DCM-MeOH (5:0 to 5:1) to give the secondary or tertiary nicotinate riboside (yields: 14-32%).

Example 9

This example exemplifies compounds prepared according to Example 8, in accordance with an embodiment of the invention.

1-((2R,3R,4S,5R)-3,4-dihydroxy-5-(hydroxymethyl)tetrahydrofuran-2-yl)-3-((neopentyloxy)carbonyl)pyridin-1-ium trifluoromethanesulfonate (5j). $^1$H NMR (500 MHz, Deuterium Oxide) δ 9.71 (d, J=1.9 Hz, 1H), 9.34 (dt, J=6.5, 1.5 Hz, 1H), 9.18 (dt, J=8.1, 1.5 Hz, 1H), 8.33 (dd, J=8.1, 6.3 Hz, 1H), 6.30 (d, J=4.4 Hz, 1H), 4.54 (dt, J=11.1, 4.1 Hz, 2H), 4.39 (t, J=4.6 Hz, 1H), 4.25-4.18 (m, 2H), 4.07 (dd, J=12.8, 2.9 Hz, 1H), 3.92 (dd, J=12.8, 3.7 Hz, 1H), 1.07 (s, 9H). $^{13}$C NMR (126 MHz, Deuterium Oxide) δ 162.83, 147.39, 143.47, 141.45, 131.10, 128.47, 99.99, 87.85, 77.52, 76.51, 69.99, 60.26, 30.84, 25.49. $^{19}$F NMR (471 MHz, Methanol-d$_4$) δ −80.11.

1-((2R,3R,4S,5R)-3,4-dihydroxy-5-(hydroxymethyl)tetrahydrofuran-2-yl)-3-((isopentyloxy)carbonyl)pyridin-1-ium trifluoromethanesulfonate (5h). $^1$H NMR (500 MHz, Methanol-d$_4$) δ 9.86 (s, 1H), 9.47 (d, J=6.2 Hz, 1H), 9.14 (dt, J=8.1, 1.5 Hz, 1H), 8.32 (dd, J=8.0, 6.2 Hz, 1H), 6.23 (d, J=4.9 Hz, 1H), 4.54 (t, J=6.8 Hz, 2H), 4.48-4.42 (m, 2H), 4.33 (dd, J=4.8, 3.1 Hz, 1H), 4.03 (dd, J=12.3, 2.7 Hz, 1H), 3.88 (dd, J=12.3, 2.2 Hz, 1H), 1.85 (dp, J=13.3, 6.7 Hz, 1H), 1.77 (q, J=6.8 Hz, 2H), 1.03 (d, J=6.6 Hz, 6H). $^{13}$C NMR (126 MHz, Deuterium Oxide) δ 162.80, 147.31, 143.48, 141.55, 131.15, 128.52, 100.05.

1-((2R,3R,4S,5R)-3,4-dihydroxy-5-(hydroxymethyl)tetrahydrofuran-2-yl)-3-(isopropoxycarbonyl)pyridin-1-ium trifluoromethanesulfonate (5g). $^1$H NMR (500 MHz, Methanol-d$_4$) δ 9.88 (t, J=1.6 Hz, 1H), 9.48 (dt, J=6.3, 1.5 Hz, 1H), 9.16 (dt, J=8.0, 1.5 Hz, 1H), 8.35 (dd, J=8.1, 6.2 Hz, 1H), 6.26 (d, J=4.7 Hz, 1H), 5.39 (hept, J=6.3 Hz, 1H), 4.53-4.44 (m, 2H), 4.37 (dd, J=4.9, 3.4 Hz, 1H), 4.07 (dd, J=12.3, 2.7 Hz, 1H), 3.92 (dd, J=12.3, 2.3 Hz, 1H), 1.49 (d, J=6.4 Hz, 6H). $^{13}$C NMR (126 MHz, Methanol-d$_4$) δ 162.20, 148.02, 144.76, 143.23, 132.72, 129.39, 102.55, 90.44, 79.85, 72.69, 72.05, 61.75, 21.85. $^{19}$F NMR (471 MHz, Methanol-d$_4$) δ −79.96.

1-((2R,3R,4S,5R)-3,4-dihydroxy-5-(hydroxymethyl)tetrahydrofuran-2-yl)-3-((tert-pentyloxy)carbonyl)pyridin-1-ium trifluoromethanesulfonate (5i). $^1$H NMR (500 MHz, Methanol-d$_4$) δ 9.80 (d, J=1.9 Hz, 1H), 9.45 (dd, J=6.3, 1.5

Hz, 1H), 9.12 (dt, J=8.1, 1.6 Hz, 1H), 8.33 (dd, J=8.1, 6.2 Hz, 1H), 6.25 (d, J=4.9 Hz, 1H), 4.49 (dd, J=6.4, 3.8 Hz, 2H), 4.36 (dd, J=4.9, 3.1 Hz, 1H), 4.05 (dd, J=12.3, 2.8 Hz, 1H), 3.91 (dd, J=12.3, 2.4 Hz, 1H), 2.05 (qd, J=7.5, 1.9 Hz, 2H), 1.68 (s, 6H), 1.06 (t, J=7.5 Hz, 3H). $^{13}$C NMR (126 MHz, Methanol-$d_4$) δ 161.53, 147.92, 144.57, 142.95, 133.58, 129.34, 102.44, 90.61, 88.53, 79.87, 72.30, 61.87, 34.34, 25.67, 25.58, 8.56. $^{19}$F NMR (471 MHz, Methanol-$d_4$) δ −82.24.

3-(tert-butoxycarbonyl)-1-((2R,3R,4S,5R)-3,4-dihydroxy-5-(hydroxymethyl)tetrahydrofuran-2-yl)pyridin-1-ium trifluoromethanesulfonate (5k). $^1$H NMR (500 MHz, Methanol-$d_4$) δ 9.81 (d, J=1.6 Hz, 1H), 9.44 (dd, J=6.3, 1.5 Hz, 1H), 9.10 (dt, J=8.1, 1.5 Hz, 1H), 8.31 (dd, J=8.1, 6.2 Hz, 1H), 6.23 (d, J=4.9 Hz, 1H), 4.46 (t, J=4.6 Hz, 2H), 4.34 (dd, J=4.8, 3.2 Hz, 1H), 4.04 (dd, J=12.2, 2.7 Hz, 1H), 3.90 (dd, J=12.2, 2.3 Hz, 1H), 1.70 (s, 9H). $^{13}$C NMR (126 MHz, Methanol-$d_4$) δ 161.64, 147.98, 144.62, 143.12, 133.72, 129.28, 102.57, 90.63, 85.95, 79.97, 72.29, 61.86, 28.16. $^{19}$F NMR (471 MHz, Methanol-$d_4$) δ −82.38.

Example 10

This example demonstrates the effect of compounds of the invention on $NAD^+$ concentration in HEK-293 cells (human embryonic kidney).

HEK-293 cells were treated with 250 μM of nicotinic acid ester mononucleotides for 24 h, and then the $NAD^+$ concentration was determined using a known $NAD^+$ cycling assay (Jacobson, E. L. et al., Arch. Biochem. Biophys., 175: 627-634 (1976)). The cells were washed with PBS, counted by haemocytometry and pelleted. The cells were then treated with 7% perchloric acid, and then neutralized with 1 M NaOH and 500 mM potassium phosphate pH 8.5. $NAD^+$ contents were then measured on a plate reader using diaphorase and lactate dehydrogenase using Resazurin as a dye that is reduced to rezarufin (emission 560 nm). $NAD^+$ levels were quantitated using a standard curve using known $NAD^+$ concentrations. $NAD^+$ concentrations are determined to nmol $NAD^+/10^6$ cells. All values in Table 1 are listed as compared to control. The compounds, concentrations thereof, and resulting $NAD^+$ levels (as a percentage of control) are set forth in Table 1.

TABLE 1

Cellular Effects of Ester Nicotinic Acid Riboside-5-phosphates on Cells

| Compound | Concentration μM | Cell Line | Incubation Time | $NAD^+$ Level (% versus control) |
|---|---|---|---|---|
| 5b (Butyl) | 25 μM | HEK293 | 24 hr | 104 ± 29 |
| 5b (Butyl) | 100 μM | HEK293 | 24 hr | 165 ± 31 |
| 5b (Butyl) | 500 μM | HEK293 | 24 hr | 103 ± 32 |
| 5c (Pentyl) | 25 μM | HEK293 | 24 hr | 80 ± 21 |
| 5c (Pentyl) | 100 μM | HEK293 | 24 hr | 105 ± 26 |
| 5c (Pentyl) | 200 μM | HEK293 | 24 hr | 171 ± 18 |
| 5c (Pentyl) | 500 μM | HEK293 | 24 hr | 124 ± 27 |
| 5d (Hexyl) | 25 μM | HEK293 | 24 hr | 136 ± 26 |
| 5d (Hexyl) | 100 μM | HEK293 | 24 hr | 162 ± 15 |
| 5d (Hexyl) | 500 μM | HEK293 | 24 hr | 146 ± 48 |
| 5e (Heptyl) | 25 μM | HEK293 | 24 hr | 152 ± 19 |
| 5e (Heptyl) | 100 μM | HEK293 | 24 hr | 150 ± 11 |
| 5e (Heptyl) | 500 μM | HEK293 | 24 hr | 123 ± 21 |
| 5f (Octyl) | 200 μM | HEK293 | 24 hr | 90 ± 8.7 |

Example 11

This example demonstrates the effect of nicotinic acid mononucleotide on intracellular $NAD^+$ levels in HEK293 and Neuro2a cells.

The ability of nicotinic acid mononucleotide, NaMN, to serve as an $NAD^+$ enhancing agent in mammalian cell lines, Neuro2a and HEK293 cells was examined after an 8 h incubation. NaMN was added to cell growth media at a concentration of 1 mM. All cell treatments were done in duplicate. Nicotinamide riboside (NR) at 1 mM concentration was performed as a positive control. Untreated cells served as negative controls. Cells were treated for the allotted time then harvested by trysin detachment and pelleting. Cells were counted by haemocytometer and then lysed by treatment with 100 μL perchloric acid (7%). Lysates were then neutralized by treatment with NaOH and $K_2PO_4$ solutions. $NAD^+$ concentrations were determined by a daphorase-based assay. $NAD^+$ standards were also run to establish a standard curve. The results are graphically depicted in FIG. 4.

Figure 1:
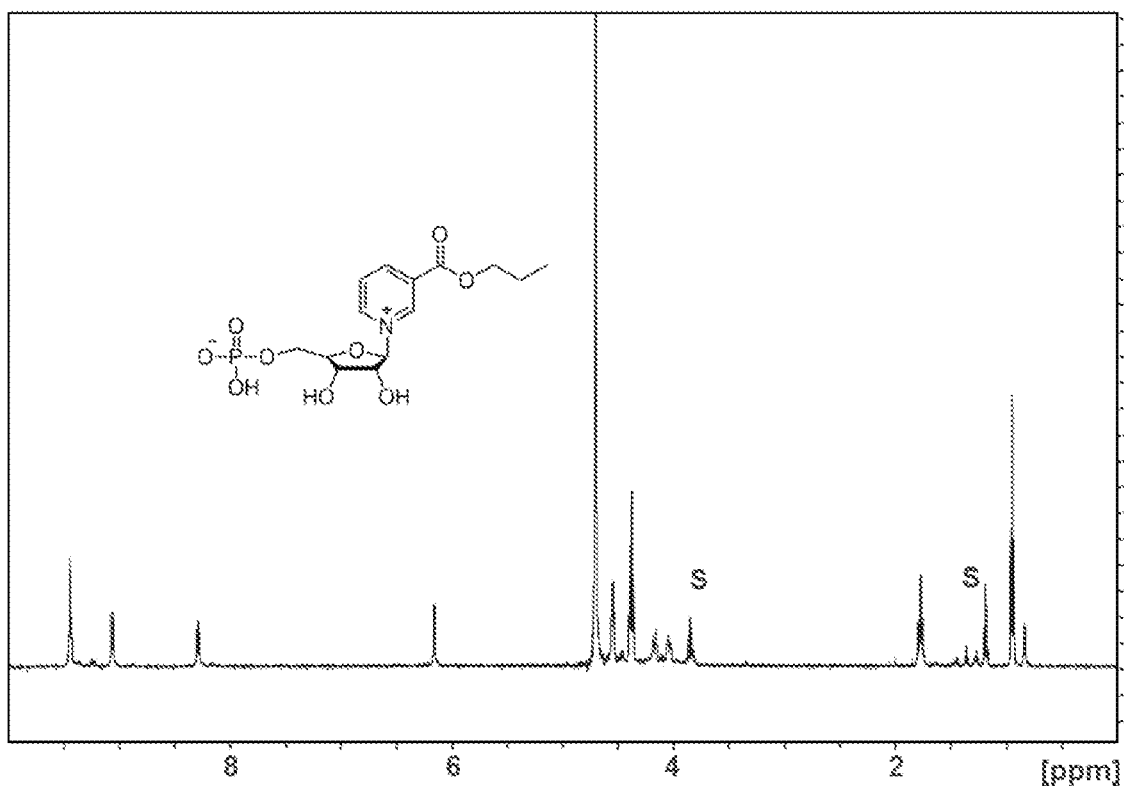
Figure 2:
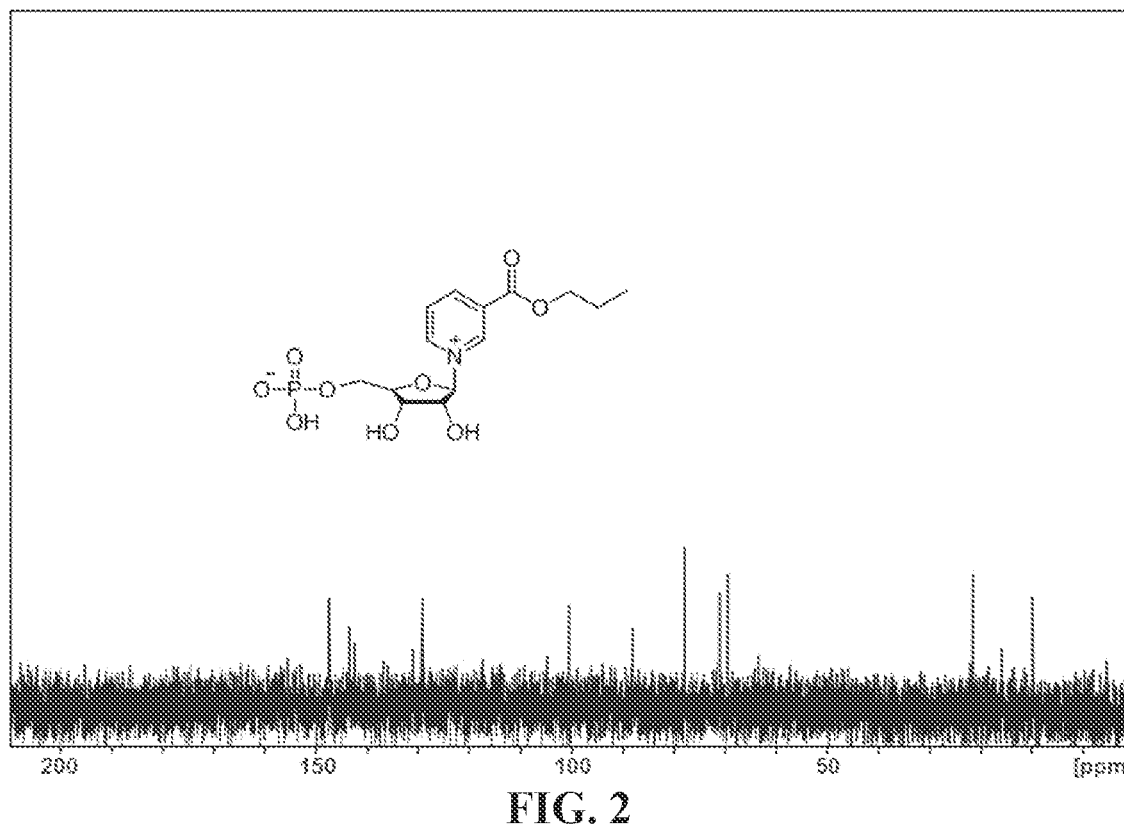
Figure 3:
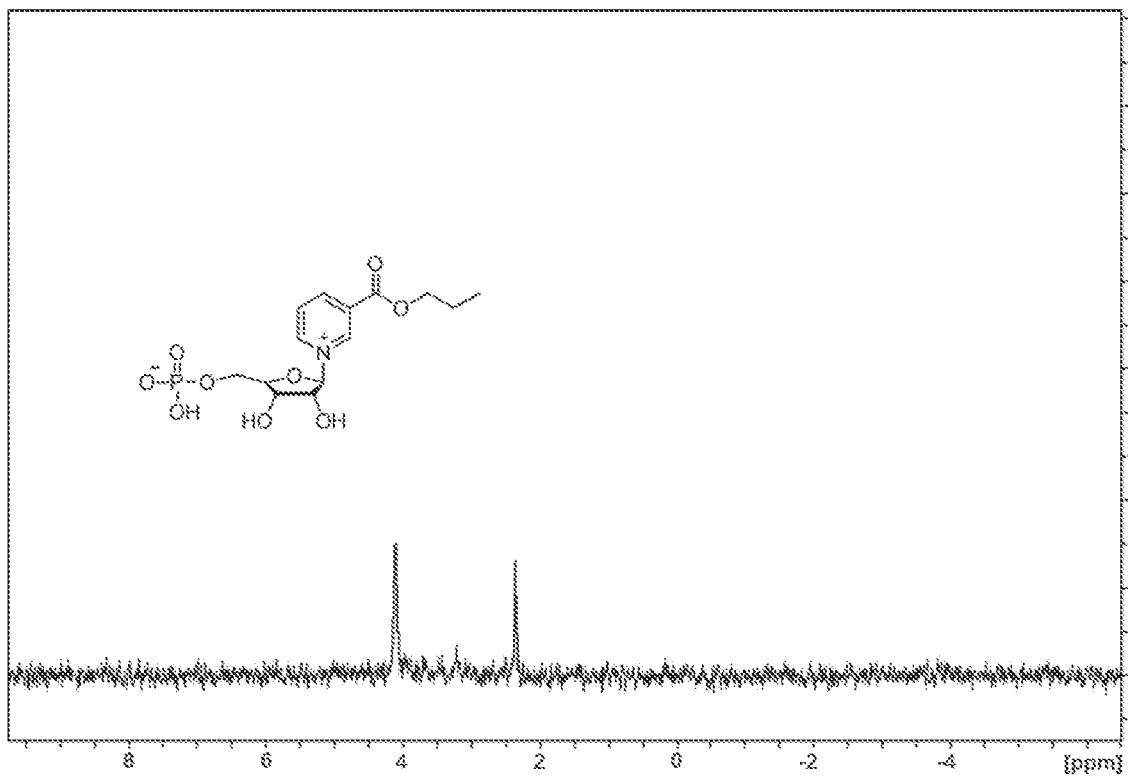
Figure 4:
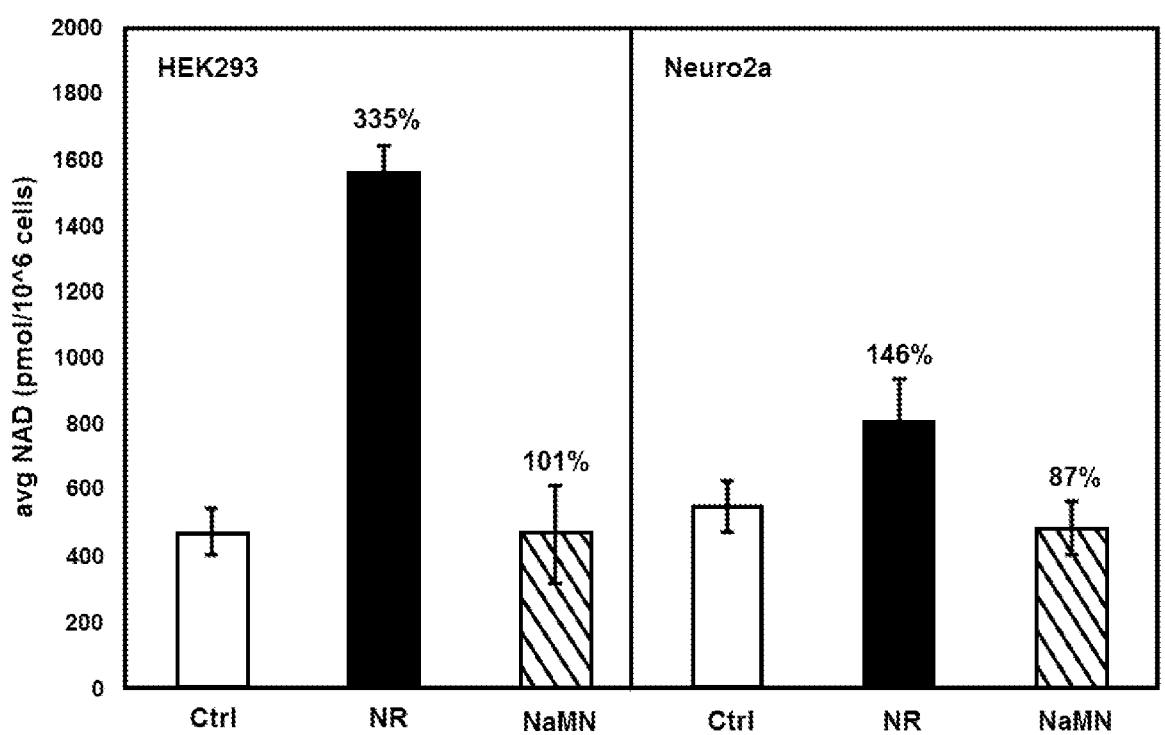
FIG. 4 is a bar graph showing the effect on intracellular levels of NAD in HEK293 and Neuro2a cells on treatment with NaMN and NR.
Figure 5A:
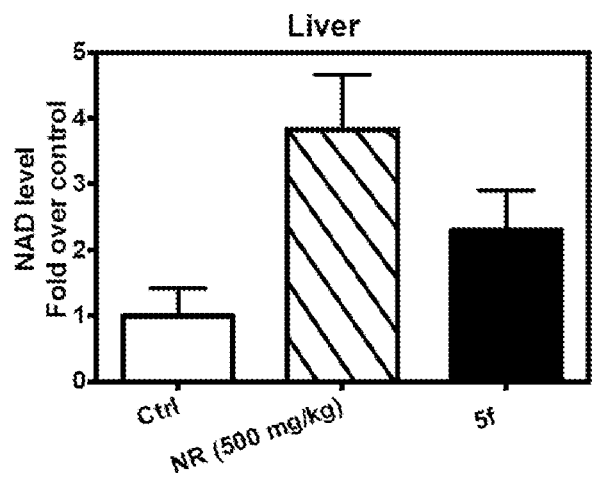
FIGS. 5A-5E are bar graphs showing NAD+ levels in liver (FIG. 5A), kidney (FIG. 5B), brain (FIG. 5C), muscle (FIG. 5D), and heart (FIG. 5E), respectively, in mice 4 h after administration of 500 mg/kg compound 5f, 500 mg/kg nicotinamide riboside, and control.
Figure 5B:
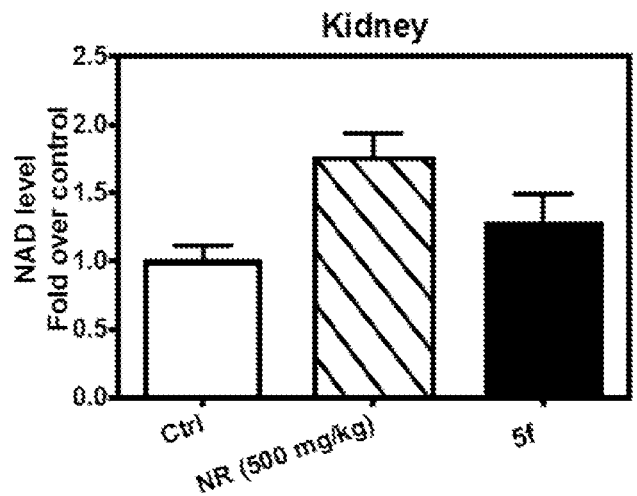
Figure 5C:
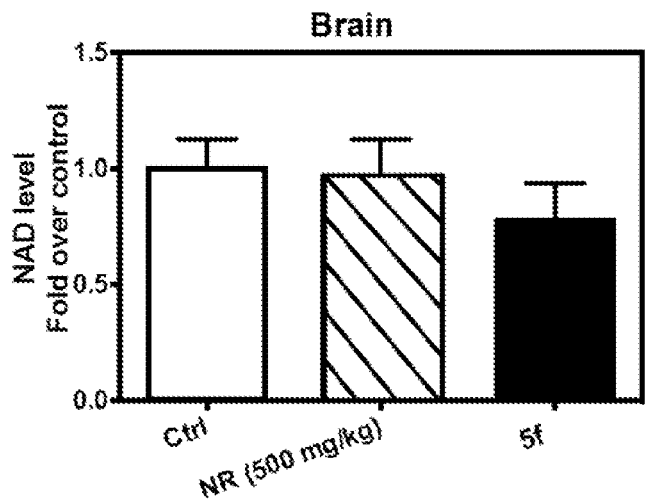
Figure 5D:
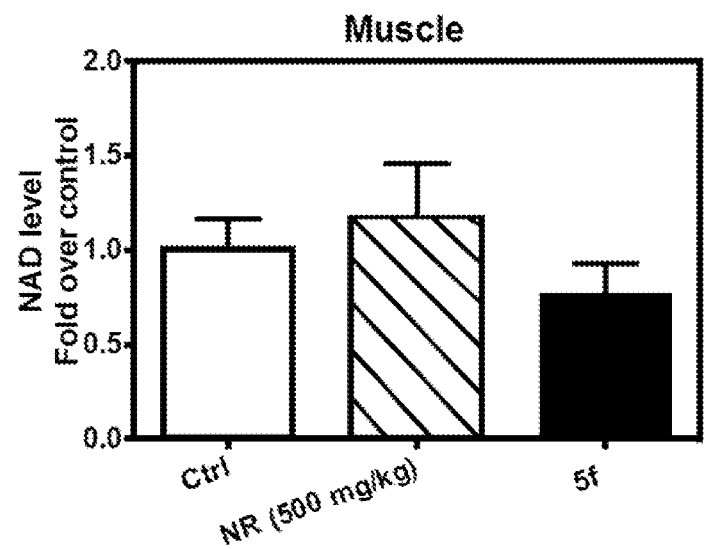
Figure 5E:
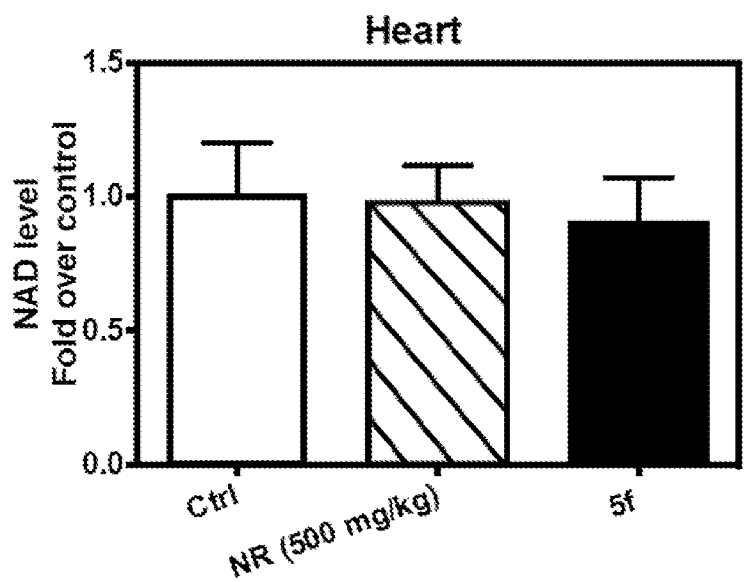

As is apparent from the results shown in FIG. 4, only NR treatment results in increased $NAD^+$ contents in cells. No intracellular increase in $NAD^+$ is observed with NaMN treatment. These results indicate that the acid compound NaMN does not appear to act as an $NAD^+$ precursor or $NAD^+$ enhancer when applied externally to mammalian cells.

Example 12

This example demonstrates the effect of the administration of inventive compounds on $NAD^+$ levels in different mouse tissues.

Mice were gavaged with either 500 mg/kg or 750 mg/kg compound dissolved in 200 μL PBS. Control mice received only 200 μL PBS. Nicotinamide riboside (NR) at the same dosage was used as a positive control. In all cases, the number of animals in each group was at least 5. After 4 hours, animals were sacrificed, and blood and tissues were harvested. For one set of experiments, mice were gavaged with compound 5f and then sacrificed after 1, 2, or 4 h. Tissues were flash frozen in tubes with liquid nitrogen. Tissue $NAD^+$ contents were measured by grinding tissues in a mortar and pestle in liquid nitrogen. Ground tissue was weighed, treated with 7% perchloric acid, and then neutralized with 1 M NaOH and 500 mM potassium phosphate at a pH of 8.5. $NAD^+$ contents were measured on a plate reader using diaphorase and lactate dehydrogenase with resazurin as a dye that is reduced to rezarufin (emission 560 nm). $NAD^+$ levels were quantitated using a standard curve using known $NAD^+$ concentrations. $NAD^+$ concentrations were determined as nmol $NAD^+/mg$ tissue.

The results are graphically depicted in FIGS. 5-10.

FIGS. 5A-5E show levels of $NAD^+$ in liver, kidney, brain, muscle, and heart, respectively, 4 h after dosing with 500 mg/kg compound 5f, 500 mg/kg NR (positive control), or control.

FIGS. 6A-6C show levels of $NAD^+$ in blood 1 h, 2 h, and 4 h, respectively, after dosing with compound 5f, 500 mg/kg NR (positive control), or control.

FIGS. 7A-7E show levels of $NAD^+$ in liver, kidney, brain, muscle, and heart, respectively, 4 h after dosing with 750 mg/kg compound 5d, 750 mg/kg compound 5c, 750 mg/kg NR (positive control), or control.

FIGS. 8A-8D show levels of NAD+ in liver, kidney, brain, and muscle, respectively, 4 h after dosing with 750 mg/kg compound 5g, 750 mg/kg compound 5a, 750 mg/kg NR (positive control), or control.

FIGS. 9A-9D show levels of NAD+ in liver, kidney, brain, and muscle, respectively, 4 h after dosing with 750 mg/kg compound 5i, 750 mg/kg compound 5h, 750 mg/kg NR (positive control), or control.

FIGS. 10A-10D show levels of NAD+ in liver, kidney, brain, and muscle, respectively, 4 h after dosing with 750 mg/kg compound 5j, 750 mg/kg compound 5k, 750 mg/kg NR (positive control), or control.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for the preparation of a compound of formula (I):

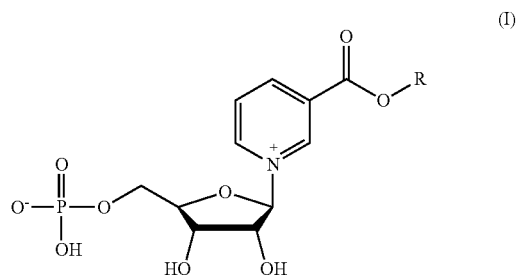

wherein R is straight or branched chain $C_3$-$C_{20}$ alkyl, straight or branched chain $C_3$-$C_{20}$ alkenyl, $C_3$-$C_{20}$ alkynyl, $C_3$-$C_{20}$ cycloalkyl, $C_6$-$C_{10}$ aryl, $C_3$-$C_{20}$ heterocyclyl, or $C_5$-$C_{10}$ heteroaryl, or a salt thereof, wherein R is substituted or unsubstituted, and wherein the process comprises the step of reacting a compound of formula (III):

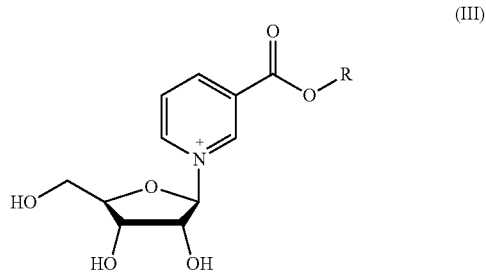

with a mixture of $POCl_3$ and $PO(OR^5)_3$, wherein $R^5$ is $C_1$-$C_6$ alkyl, followed by isolation of the compound of formula (I).

2. The process of claim 1, wherein R is n-propyl.

3. The process of claim 1, wherein the compound of formula (III) is prepared by reacting a compound of formula (II):

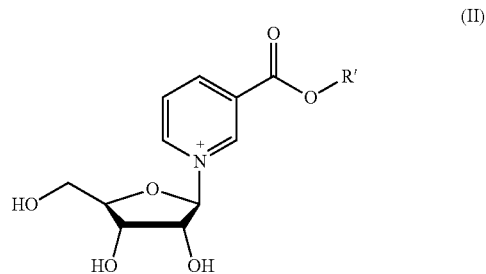

wherein R' is methyl or ethyl, with a compound of formula ROH in the presence of a base in a solvent to form the compound of formula (III).

4. The process of claim 3, wherein the base is potassium t-butoxide, the solvent is ROH, or the base is potassium t-butoxide and the solvent is ROH.

5. The process of claim 1, wherein the compound of formula (III) is prepared by reacting a nicotinate ester (IV):

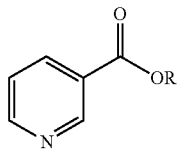
(IV)

with 1,2,3,4-tetra-O-acetyl-D-ribofuranose to provide a compound of formula (V):

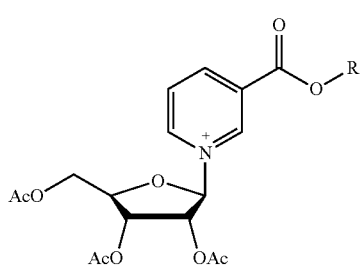
(V)

and reacting the compound of formula (V) with a base to form the compound of formula (III).

6. A compound of formula (I):

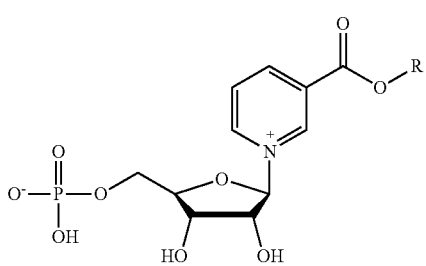
(I)

wherein R is n-propyl, n-butyl, n-pentyl, n-hexyl, n-heptyl, n-octyl, 2,2-dimethylpropyl, 3-methylbutyl, isopropyl, 1,1-dimethylpropyl, t-butyl, substituted or unsubstituted morpholine, substituted or unsubstituted piperidine, substituted or unsubstituted tetrahydrofuryl, substituted or unsubstituted oxetanyl, substituted or unsubstituted pyrrolidinyl, or substituted or unsubstituted dihydrobenzofuran, or a salt thereof.

7. A pharmaceutical composition comprising the compound or salt of claim 6 and a pharmaceutically acceptable carrier.

8. A nutraceutical composition comprising a compound or salt of claim 6.

9. A method for increasing cell $NAD^+$ production comprising administering to a cell a compound of claim 6 or a salt thereof.

10. The method of claim 9, wherein the cell is in a mammal having a lipid disorder, a metabolic dysfunction, a cardiovascular disease, CNS or PNS trauma, a neurodegenerative disease or condition, or hearing loss, or is in a mammal that has been exposed to a toxic agent.

11. The method of claim 9, wherein the cell is in a mammal, wherein the compound is administered in an amount effective for promoting the function of the metabolic system, promoting muscle function or recovery, promoting the function of the auditory system, or promoting cognitive function.

12. A method of improving mitochondrial densities in a cell, wherein the method comprises administering to the cell a compound of claim 6 or a salt thereof.

13. The method of claim 12, wherein the cell is in a mammal having a lipid disorder, a metabolic dysfunction, a cardiovascular disease, CNS or PNS trauma, a neurodegenerative disease or condition, hearing loss, or is in a mammal that has been exposed to a toxic agent.

14. The method of claim 12, wherein the cell is in a mammal at risk for hearing loss.

15. The method of claim 12, wherein the cell is in a mammal, wherein the compound is administered in an amount effective for promoting the function of the metabolic system, promoting muscle function or recovery, promoting the function of the auditory system, or promoting cognitive function.

16. The process of claim 1, wherein R is n-butyl, n-pentyl, n-hexyl, n-heptyl, n-octyl, 2,2-dimethylpropyl, 3-methylbutyl, isopropyl, 1,1-dimethylpropyl, or t-butyl.

17. The process of claim 3, wherein R is n-propyl.

18. The process of claim 1, wherein R is substituted or unsubstituted $C_3$-$C_{20}$ heterocyclyl.

19. The process of claim 18, wherein the substituted or unsubstituted $C_3$-$C_{20}$ heterocyclyl is selected from substituted or unsubstituted morpholine, substituted or unsubstituted piperidine, substituted or unsubstituted tetrahydrofuryl, substituted or unsubstituted oxetanyl, substituted or unsubstituted pyrrolidinyl, and substituted or unsubstituted dihydrobenzofuran.

20. The process of claim 19, wherein the substitution comprises 1, 2, 3, 4, or 5 substituents independently selected from alkyl, halo, or aryl.

21. The compound of claim 6, wherein:
R is substituted or unsubstituted morpholine, substituted or unsubstituted piperidine, substituted or unsubstituted tetrahydrofuryl, substituted or unsubstituted oxetanyl, substituted or unsubstituted pyrrolidinyl, or substituted or unsubstituted dihydrobenzofuran, or a salt thereof; and optionally, the substitution comprises 1, 2, 3, 4, or 5 substituents independently selected from alkyl, halo, or aryl.

22. The compound of claim 6, wherein R is n-propyl.

23. The method of claim 9, wherein R is n-propyl.

24. The method of claim 12, wherein R is n-propyl.

* * * * *